US006511811B1

(12) United States Patent
Olefsky et al.

(10) Patent No.: US 6,511,811 B1
(45) Date of Patent: *Jan. 28, 2003

(54) PROTEIN KINASE C ANTAGONIST RELATED TO INSULIN RECEPTOR

(75) Inventors: Jerrold M. Olefsky, Solana Beach; Tahir S. Pillay, San Diego, both of CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 31 days.

(21) Appl. No.: 08/485,393

(22) Filed: Jun. 7, 1995

(51) Int. Cl.$^7$ .......................... C07K 7/02; C07K 14/71; C12Q 1/00
(52) U.S. Cl. .......................... 435/7.1; 435/7.2; 435/183; 530/300; 530/326; 530/327; 530/350
(58) Field of Search ................................. 530/300, 350, 530/327, 326; 514/2, 15; 435/183, 4, 7.1

(56) References Cited

U.S. PATENT DOCUMENTS

| | | | | |
|---|---|---|---|---|
| 4,952,567 A | * | 8/1990 | DeMeyts et al. | .............. 514/54 |
| 5,292,662 A | | 3/1994 | Sandmeyer | ............... 435/320.1 |
| 5,399,346 A | | 3/1995 | Anderson et al. | ......... 424/93.21 |
| 5,545,636 A | * | 8/1996 | Heath, Jr. et al. | ............ 514/214 |

FOREIGN PATENT DOCUMENTS

| | | |
|---|---|---|
| GB | 1556149 | 4/1977 |

OTHER PUBLICATIONS

Upstate Biotechnology, Certificate of analysis of protein kinase C inhibitor peptide (19–31), May 1997.*

Zachayus et al., Protein kinase C and insulin receptor beta–subunit serine phosphorylation in cultured foetal rat hepatocytes, Mol. Cell. Endocrinol., 105: 11–20, 1994.*

Girault, Protein Kinases and Phosphotases, Neurotransmissions, X(3): 1–5, Oct. 1994.*

Chin et al., Activation of protein kinase Calpha inhibits insulin-stimulated tyrosine phosphorylation of insulin receptor substrate–1, Mol. Endocrinol., 8: 51–58, Jan. 1994.*

Smith et al., Specificities of autoinhibitory domain peptides for four protein kinases, J. Biol. Chem., 265(4): 1837–1840, Feb. 1990.*

Berti, Lucia et al., "Glucose–induced Translocation of Protein Kinase C Isoforms in Rat–1 Fibroblasts Is Paralleled by Inhibition of the Insulin Receptor Tyrosine Kinase," *The Journal of Biological Chemistry*, vol. 269, No. 5, Feb. 4, 1994, pp. 3381–3386.

Carter, Wayne G. et al., "Studies into the Identity of the Sites of Insulin–Stimulated Insulin Receptor Serine Phosphorylation. Characterization of Synthetic Peptide Substrates for the Insulin–Stimulated Insulin Receptor Serine Kinase," *Biochemistry*, vol. 34, pp. 9488–9499, 1995.

Mosthaf, Luitgard et al., C–terminus or Juxtamembrane Deletions in the Insulin Receptor Do Not Affect the Glucose–dependent Inhibition of the Tyrosine Kinase Activity, *Eur. J. Biochem.*, vol. 227, pp. 787–791, 1995.

Kellerer et al., "Mechanism of Insulin Receptor Kinase Inhibition in Non–Insulin–dependent Diabetes Mellitus Patients", *J. Clin. Invest.*, 96, 6–11 (1995).

Brady et al., 1979, "Practical Synthesis of Cyclic Peptides, with an Example of Dependence of Cyclization Yield upon Linear Sequence," *J. Org. Chem.* 44(18):3101–3105.

Gorman et al., 1982, "The Rous sarcoma virus long terminal repeat is a strong promoter when introduced into a variety of eukaryotic cells by DNA–mediated transfection," *Proc. Natl. Acad. Sci. USA* 79:6777–6781.

Deamer et al., "Liposome Preparation: Methods and Mechanisms," 1983, *Liposomes, Marcel Dekker*, New York, pp. 27–51.

Boshart et al., "A Very Strong Enhancer Is Located Upstream of an Immediate Early Gene of Human Cytomegalovirus," 1985, *Cell* 41:521–530.

Ullrich et al., "Human insulin receptor and its relationship to the tyrosine kinase family of oncogenes," 1985, *Nature* 313:756–761.

Hope et al., "Generation of Multilamellar and Unilamellar Phospholipid Vesicles," 1986, *Chem. Phys. Lipids* 40:89–107.

Caro et al., "Studies on the Mechanism of Insulin Resistance in the Liver from Humans with Noninsulin–dependent Diabetes," 1986, *J. Clin. Invest.* 78:249–258.

Caro et al., "Insulin Receptor Kinase in Human Skeletal Muscle from Obese Subjects with and without Noninsulin Dependent Diabetes," 1987, *J. Clin. Invest.* 79:1330–1337.

Comi et al., "Relationship of Insulin Binding and Insulin–stimulated Tyrosine Kinase Activity is Altered in Type II Diabetes," 1987, *J. Clin. Invest.* 79:453–462.

McClain et al., "A Mutant Insulin Receptor with Defective Tyrosine Kinase Displays No Biologic Activity and Does Not Undergo Endocytosis," 1987, *J. Biol. Chem.* 262(30):14663–14671.

(List continued on next page.)

Primary Examiner—Lorraine Spector
Assistant Examiner—Claire M. Kaufman
(74) Attorney, Agent, or Firm—Gray Cary Ware & Freidenrich LLP; Lisa A. Haile

(57) ABSTRACT

Methods and compositions are provided for the treatment of insulin-resistance through the inhibition of protein kinase C-mediated phosphorylation of the amino acid residue $Ser_{1270}$ of the insulin receptor. Methods for testing candidate compounds suitable for inhibition of serine-phosphorylation by protein kinase C are also provided.

13 Claims, 13 Drawing Sheets

OTHER PUBLICATIONS

Freidenberg et al., "Decreased Kinase of Insulin Receptors from Adipocytes of Non–insulin–dependent Diabetic Subjects, " 1987, *J. Clin. Invest.* 79:240–250.

Takayama et al., "Phorbol Ester–induced Serine Phosphorylation of the Insulin Receptor Decreases its Tyrosine Kinase Activity," 1988, *J. Biol. Chem.* 262(7):3440–3447.

Maegawa et al., "Properties of a Human Inslin Receptor with a COOH–terminal Truncation," 1988, *J. Biol. Chem.* 263(18):8912–8917.

McClain et al., "Properties of a Human Insulin Receptor with a COOH–terminal Truncation," 1988, *J. Biol. Chem.* 262(18):8904–8911.

Brillon et al., "Mechanism of Defective Insulin–Receptor Kinase Activity in NIDDM," 1989, *Diabetes* 38:397–403.

Rotter et al., 1990, *Diabetes Mellitus: Theory and Practice*, Chapter 24, Rifkin et al., New York, Elsevier, pp. 378–413.

Yki–Jä rvinen, "Acute and chronic effects of hyperglycaemia on glucose metabolism," 1990, *Diabetologia* 33:579–585.

Lewis et al., "Threonine 1336 of the Human Insulin Receptor Is a Major Target for Phosphorylation by Protein Kinase C," 1990, Biochemistry 29(7):1807–1812.

Thies et al., "Insulin–Receptor Autophosphorylation and Endogenous Substrate Phosphorylation in Human Adipocytes From Control, Obese, and NIDDM Subjects," 1990, *Diabetes* 39:250–259.

Maegawa et al., "Impaired Autophosphorylation of Insulin Receptors from Abdominal Skeletal Muscles in Nonobese Subjects With NIDDM," 1991 *Diabetes* 40:815–819.

Anderson et al., "Phorbol Ester–mediated Protein Kinase C Interaction with Wild–type and COOH–terminal Truncated Insulin Receptors," 1991, *J. Biol. Chem.* 266(12):21760–21764.

Clark–Lewis et al., "Chemical Synthesis, Purifcation and Characterization of Two Inflammtory Proteins, Neutrophil Activating Peptide 1 (Interleukin–8) and Neutrophil Activating Peptide 2," 1991, *Biochemistry* 30:3128–3135.

Müller et al., "Prevention by Protein Kinase C Inhibitors of Glucose–Induced Insulin–Receptor Tyrosine Kinase Resistance in Rat Fat Cells," 1991, *Diabetes* 40:1440–1448.

Yki–Järvinen, "Glucose Toxicity," 1992, *Endocrine Rev.* 13:415–431.

Seely et al., 1993, *Insulin resistance and its clinical disorders*, Chapter 7, Moller, Ed., England, John Wile & Sons, Ltd., pp. 187–252.

Fynan et al., "DNA vaccines: Protective immunizations by parenteral, mucosal, and gene–gun inoculations," 1993, *Proc. Natl. Acad. Sci. USA* 90:11478–11482.

Clark–Lewis et al., "Platelet factor 4 binds to interleukin 8 receptors and activates neutrophils when its N terminus is modified with Glu–Leu–Arg," 1993, *Proc. Natl. Acad. Sci. USA* 90:3574–3577.

Cavelier–Frontin et al., "How to perform small peptide cyclizations," 1993, *J. Mol. Structure* 286:125–130.

Saad et al., "Regulation of Insulin Receptor, Insulin Receptor Substrate–1 and Phosphatidylinositol 3–Kinase in 3T3–F442A Adipocytes. Effects of Differentiation, Insulin, and Dexamethasone," 1994, *Mol. Endocrinol.* 8(5):545–557.

Mergler, "Synthesis of Fully Protected Peptide Fragments," 1994, *Meth. Mol. Biol.* 90:287–301.

Nolan et al., "Role of Human Skeletal Muscle Insulin Receptor Kinase in the *in Vivo* Insulin Resistance of Non-insulin–Dependent Diabetes Mellitus and Obesity," 1994, *J. Clin. Endocrinol. Metab.* 78:471–477.

Sasaoka et al., "Evidence for Functional Role of Shc Proteins in Mitogenic Signaling Induced by Insulin, Insulin–like Growth Factor–1, and Epidermal Growth Factor," 1994, *J. Biol. Chem.* 269(18):13689–13694.

McMurray et al., "Influence of Solid Support, Solvent and Coupling Reagent on the Head–to Tail Cyclization of Res-in–Bound Peptides," 1994, *Peptide Res.* 7:195.

Kates et al., "A Novel, Convenient, Three–Dimensional Orthogonal Strategy for Solid–Phase Synthesis of Cyclic Peptides[1–3]," 1995, *Tetrahedron Lett*, 34:1549–1552.

\* cited by examiner

```
AGA AAG AGG CAG CCA GAT GGG CCG CTG GGA CCG CTT TAC GCT TCT TCA
Arg Lys Arg Gln Pro Asp Gly Pro Leu Gly Pro Leu Tyr Ala Ser Ser>

AAC CCT GAG TAT CTC AGT GCC AGT GAT GTG TTT CCA TGC TCT GTG TAC
Asn Pro Glu Tyr Leu Ser Ala Ser Asp Val Phe Pro Cys Ser Val Tyr>

GTG CCG GAC GAG TGG GAG GTG TCT CGA GAG AAG ATC ACC CTC CTT CGA
Val Pro Asp Glu Trp Glu Val Ser Arg Glu Lys Ile Thr Leu Leu Arg>

GAG CTG GGG CAG GGC TCC TTC GGC ATG GTG TAT GAG GGC AAT GCC AGG
Glu Leu Gly Gln Gly Ser Phe Gly Met Val Tyr Glu Gly Asn Ala Arg>

GAC ATC ATC AAG GGT GAG GCA GAG ACC CGC GTG GCG GTG AAG ACG GTC
Asp Ile Ile Lys Gly Glu Ala Glu Thr Arg Val Ala Val Lys Thr Val>

AAC GAG TCA GCC AGT CTC CGA GAG CGG ATT GAG TTC CTC AAT GAG GCC
Asn Glu Ser Ala Ser Leu Arg Glu Arg Ile Glu Phe Leu Asn Glu Ala>

TCG GTC ATG AAG GGC TTC ACC TGC CAT CAC GTG GTG CGC CTC CTG GGA
Ser Val Met Lys Gly Phe Thr Cys His His Val Val Arg Leu Leu Gly>

GTG GTG TCC AAG GGC CAG CCC ACG CTG GTG GTG ATG GAG CTG ATG GCT
Val Val Ser Lys Gly Gln Pro Thr Leu Val Val Met Glu Leu Met Ala>

CAC GGA GAC CTG AAG AGC TAC CTC CGT TCT CTG CGG CCA GAG GCT GAG
His Gly Asp Leu Lys Ser Tyr Leu Arg Ser Leu Arg Pro Glu Ala Glu>

AAT AAT CCT GGC CGC CCT CCC CCT ACC CTT CAA GAG ATG ATT CAG ATG
Asn Asn Pro Gly Arg Pro Pro Pro Thr Leu Gln Glu Met Ile Gln Met>
```

FIG. 2A

```
GCG GCA GAG ATT GCT GAC GGG ATG GCC TAC CTG AAC GCC AAG AAG TTT
Ala Ala Glu Ile Ala Asp Gly Met Ala Tyr Leu Asn Ala Lys Lys Phe>

GTG CAT CGG GAC CTG GCA GCG AGA AAC TGC ATG GTC GCC CAT GAT TTT
Val His Arg Asp Leu Ala Ala Arg Asn Cys Met Val Ala His Asp Phe>

ACT GTC AAA ATT GGA GAC TTT GGA ATG ACC AGA GAC ATC TAT GAA ACG
Thr Val Lys Ile Gly Asp Phe Gly Met Thr Arg Asp Ile Tyr Glu Thr>

GAT TAC TAC CGG AAA GGG GGC AAG GGT CTG CTC CCT GTA CGG TGG ATG
Asp Tyr Tyr Arg Lys Gly Gly Lys Gly Leu Leu Pro Val Arg Trp Met>

GCA CCG GAG TCC CTG AAG GAT GGG GTC TTC ACC ACT TCT TCT GAC ATG
Ala Pro Glu Ser Leu Lys Asp Gly Val Phe Thr Thr Ser Ser Asp Met>

TGG TCC TTT GGC GTG GTC CTT TGG GAA ATC ACC AGC TTG GCA GAA CAG
Trp Ser Phe Gly Val Val Leu Trp Glu Ile Thr Ser Leu Ala Glu Gln>

CCT TAC CAA GGC CTG TCT AAT GAA CAG GTG TTG AAA TTT GTC ATG GAT
Pro Tyr Gln Gly Leu Ser Asn Glu Gln Val Leu Lys Phe Val Met Asp>

GGA GGG TAT CTG GAT CAA CCC GAC AAC TGT CCA GAG AGA GTC ACT GAC
Gly Gly Tyr Leu Asp Gln Pro Asp Asn Cys Pro Glu Arg Val Thr Asp>

CTC ATG CGC ATG TGC TGG CAA TTC AAC CCC AAG ATG AGG CCA ACC TTC
Leu Met Arg Met Cys Trp Gln Phe Asn Pro Lys Met Arg Pro Thr Phe>

CTG GAG ATT GTC AAC CTG CTC AAG GAC GAC CTG CAC CCC AGC TTT CCA
Leu Glu Ile Val Asn Leu Leu Lys Asp Asp Leu His Pro Ser Phe Pro>
```

FIG. 2B

```
GAG GTG TCG TTC TTC CAC AGC GAG GAG AAC AAG GCT CCC GAG AGT GAG
Glu Val Ser Phe Phe His Ser Glu Glu Asn Lys Ala Pro Glu Ser Glu>

GAG CTG GAG ATG GAG TTT GAG GAC ATG GAG AAT GTG CCC CTG GAC CGT
Glu Leu Glu Met Glu Phe Glu Asp Met Glu Asn Val Pro Leu Asp Arg>

TCC TCG CAC TGT CAG AGG GAG GAG GCG GGG GGC CGG GAT GGA GGG TCC
Ser Ser His Cys Gln Arg Glu Glu Ala Gly Gly Arg Asp Gly Gly Ser>

TCG CTG GGT TTC AAG CGG AGC TAC GAG GAA CAC ATC CCT TAC ACA CAC
Ser Leu Gly Phe Lys Arg Ser Tyr Glu Glu His Ile Pro Tyr Thr His>

ATG AAC GGA GGC AAG AAA AAC GGG CGG ATT CTG ACC TTG CCT CGG TCC
Met Asn Gly Gly Lys Lys Asn Gly Arg Ile Leu Thr Leu Pro Arg Ser>

AAT CCT TCC TAA    (SEQ ID NO:3)
Asn Pro Ser ***>   (SEQ ID NO:4)
```

R K R Q P D G P L G P L Y A S S N P E Y L S A S D V F P C S
V Y V P D E W E V S R E K I T L L R E L G Q G S F G M V Y E
G N A R D I I K G E A E T R V A V $^{1030}$ <u>K T V N E S A S L R</u>
<u>E</u>$^{1040}$ R I E F L N E A S V M K G F T C H H V V R L L G V V S K
G Q P T L V V M E L M A H G D L K S Y L R S L R P E A E N N
P G R P P P T L Q E M I Q M A A E I A D G M A Y L N A K K F
V H R D L A A R N C M V A H D F T V K I G D F G M T R D I Y
E T D Y Y R K G G K G L L P V R W M A P E S L K D G V F T T
S S D M W S F G V V L W E I T S L A E Q P Y Q G L S N E Q V
L K F V M D G G Y L D Q P D N C P E R V T D L M R M C W Q F
N P K M R P T F L E I V N L L K $^{1265}$ <u>P P L H P</u> [S] <u>F P E V</u>
<u>S</u>$^{1275}$ F F H S E E N K A P E S E E L E M E F E D M E N V P L D
R S S H C Q R E E A G G R D G G S S L G F K R S Y E E H I P
Y T H M N G G K K N G R I L T L P R S N P S 1355 (SEQ ID NO:4)

SEQUENCE LISTING

<160> NUMBER OF SEQ ID NOS: 6

<210> SEQ ID NO 1
<211> LENGTH: 11
<212> TYPE: PRT
<213> ORGANISM: Homo sapiens

<400> SEQUENCE: 1

```
Asp Asp Leu His Pro Ser Phe Pro Glu Val Ser
 1               5                  10
```

```
<210> SEQ ID NO 2
<211> LENGTH: 33
<212> TYPE: DNA
<213> ORGANISM: Homo sapiens

<400> SEQUENCE: 2
gacgacctgc accccagctt tccagaggtg tcg                              33

<210> SEQ ID NO 3
<211> LENGTH: 1212
<212> TYPE: DNA
<213> ORGANISM: Homo sapiens
<220> FEATURE:
<221> NAME/KEY: CDS
<222> LOCATION: (1)...(1209)

<400> SEQUENCE: 3
```

```
aga aag agg cag cca gat ggg ccg ctg gga ccg ctt tac gct tct tca    48
Arg Lys Arg Gln Pro Asp Gly Pro Leu Gly Pro Leu Tyr Ala Ser Ser
 1               5                  10                  15 aac cct gag tat ctc agt gcc agt gat gtg ttt cca tgc tct gtg tac    96
Asn Pro Glu Tyr Leu Ser Ala Ser Asp Val Phe Pro Cys Ser Val Tyr
                20                  25                  30 gtg ccg gac gag tgg gag gtg tct cga gag aag atc acc ctc ctt cga   144
Val Pro Asp Glu Trp Glu Val Ser Arg Glu Lys Ile Thr Leu Leu Arg
            35                  40                  45 gag ctg ggg cag ggc tcc ttc ggc atg gtg tat gag ggc aat gcc agg   192
Glu Leu Gly Gln Gly Ser Phe Gly Met Val Tyr Glu Gly Asn Ala Arg
 50                  55                  60 gac atc atc aag ggt gag gca gag acc cgc gtg gcg gtg aag acg gtc   240
Asp Ile Ile Lys Gly Glu Ala Glu Thr Arg Val Ala Val Lys Thr Val
 65                  70                  75                  80 aac gag tca gcc agt ctc cga gag cgg att gag ttc ctc aat gag gcc   288
Asn Glu Ser Ala Ser Leu Arg Glu Arg Ile Glu Phe Leu Asn Glu Ala
                85                  90                  95 tcg gtc atg aag ggc ttc acc tgc cat cac gtg gtg cgc ctc ctg gga   336
Ser Val Met Lys Gly Phe Thr Cys His His Val Val Arg Leu Leu Gly
                100                 105                 110 gtg gtg tcc aag ggc cag ccc acg ctg gtg gtg atg gag ctg atg gct   384
Val Val Ser Lys Gly Gln Pro Thr Leu Val Val Met Glu Leu Met Ala
            115                 120                 125 cac gga gac ctg aag agc tac ctc cgt tct ctg cgg cca gag gct gag   432
His Gly Asp Leu Lys Ser Tyr Leu Arg Ser Leu Arg Pro Glu Ala Glu
        130                 135                 140 aat aat cct ggc cgc cct ccc cct acc ctt caa gag atg att cag atg   480
Asn Asn Pro Gly Arg Pro Pro Pro Thr Leu Gln Glu Met Ile Gln Met
145                 150                 155                 160 gcg gca gag att gct gac ggg atg gcc tac ctg aac gcc aag aag ttt   528
Ala Ala Glu Ile Ala Asp Gly Met Ala Tyr Leu Asn Ala Lys Lys Phe
                165                 170                 175 gtg cat cgg gac ctg gca gcg aga aac tgc atg gtc gcc cat gat ttt   576
Val His Arg Asp Leu Ala Ala Arg Asn Cys Met Val Ala His Asp Phe
                180                 185                 190 act gtc aaa att gga gac ttt gga atg acc aga gac atc tat gaa acg   624
Thr Val Lys Ile Gly Asp Phe Gly Met Thr Arg Asp Ile Tyr Glu Thr
            195                 200                 205 gat tac tac cgg aaa ggg ggc aag ggt ctg ctc cct gta cgg tgg atg   672
Asp Tyr Tyr Arg Lys Gly Gly Lys Gly Leu Leu Pro Val Arg Trp Met
```

```
              210                 215                 220
gca ccg gag tcc ctg aag gat ggg gtc ttc acc act tct tct gac atg      720
Ala Pro Glu Ser Leu Lys Asp Gly Val Phe Thr Thr Ser Ser Asp Met
225                 230                 235                 240 tgg tcc ttt ggc gtg gtc ctt tgg gaa atc acc agc ttg gca gaa cag      768
Trp Ser Phe Gly Val Val Leu Trp Glu Ile Thr Ser Leu Ala Glu Gln
                    245                 250                 255 cct tac caa ggc ctg tct aat gaa cag gtg ttg aaa ttt gtc atg gat      816
Pro Tyr Gln Gly Leu Ser Asn Glu Gln Val Leu Lys Phe Val Met Asp
                260                 265                 270 gga ggg tat ctg gat caa ccc gac aac tgt cca gag aga gtc act gac      864
Gly Gly Tyr Leu Asp Gln Pro Asp Asn Cys Pro Glu Arg Val Thr Asp
            275                 280                 285 ctc atg cgc atg tgc tgg caa ttc aac ccc aag atg agg cca acc ttc      912
Leu Met Arg Met Cys Trp Gln Phe Asn Pro Lys Met Arg Pro Thr Phe
290                 295                 300 ctg gag att gtc aac ctg ctc aag gac gac ctg cac ccc agc ttt cca      960
Leu Glu Ile Val Asn Leu Leu Lys Asp Asp Leu His Pro Ser Phe Pro
305                 310                 315                 320 gag gtg tcg ttc ttc cac agc gag gag aac aag gct ccc gag agt gag     1008
Glu Val Ser Phe Phe His Ser Glu Glu Asn Lys Ala Pro Glu Ser Glu
                325                 330                 335 gag ctg gag atg gag ttt gag gac atg gag aat gtg ccc ctg gac cgt     1056
Glu Leu Glu Met Glu Phe Glu Asp Met Glu Asn Val Pro Leu Asp Arg
            340                 345                 350 tcc tcg cac tgt cag agg gag gag gcg ggg ggc cgg gat gga ggg tcc     1104
Ser Ser His Cys Gln Arg Glu Glu Ala Gly Gly Arg Asp Gly Gly Ser
        355                 360                 365 tcg ctg ggt ttc aag cgg agc tac gag gaa cac atc cct tac aca cac     1152
Ser Leu Gly Phe Lys Arg Ser Tyr Glu Glu His Ile Pro Tyr Thr His
370                 375                 380 atg aac gga ggc aag aaa aac ggg cgg att ctg acc ttg cct cgg tcc     1200
Met Asn Gly Gly Lys Lys Asn Gly Arg Ile Leu Thr Leu Pro Arg Ser
385                 390                 395                 400 aat cct tcc taa                                                     1212
Asn Pro Ser <210> SEQ ID NO 4
<211> LENGTH: 403
<212> TYPE: PRT
<213> ORGANISM: Homo sapiens

<400> SEQUENCE: 4

Arg Lys Arg Gln Pro Asp Gly Pro Leu Gly Pro Leu Tyr Ala Ser Ser
 1               5                  10                  15

Asn Pro Glu Tyr Leu Ser Ala Ser Asp Val Phe Pro Cys Ser Val Tyr
                20                  25                  30

Val Pro Asp Glu Trp Glu Val Ser Arg Glu Lys Ile Thr Leu Leu Arg
            35                  40                  45

Glu Leu Gly Gln Gly Ser Phe Gly Met Val Tyr Glu Gly Asn Ala Arg
        50                  55                  60

Asp Ile Ile Lys Gly Glu Ala Glu Thr Arg Val Ala Val Lys Thr Val
65                  70                  75                  80

Asn Glu Ser Ala Ser Leu Arg Glu Arg Ile Glu Phe Leu Asn Glu Ala
                85                  90                  95

Ser Val Met Lys Gly Phe Thr Cys His His Val Val Arg Leu Leu Gly
                100                 105                 110

Val Val Ser Lys Gly Gln Pro Thr Leu Val Val Met Glu Leu Met Ala
```

```
                115                 120                 125
His Gly Asp Leu Lys Ser Tyr Leu Arg Ser Leu Arg Pro Glu Ala Glu
        130                 135                 140

Asn Asn Pro Gly Arg Pro Pro Thr Leu Gln Glu Met Ile Gln Met
145                 150                 155                 160

Ala Ala Glu Ile Ala Asp Gly Met Ala Tyr Leu Asn Ala Lys Lys Phe
                165                 170                 175

Val His Arg Asp Leu Ala Ala Arg Asn Cys Met Val Ala His Asp Phe
                180                 185                 190

Thr Val Lys Ile Gly Asp Phe Gly Met Thr Arg Asp Ile Tyr Glu Thr
                195                 200                 205

Asp Tyr Tyr Arg Lys Gly Gly Lys Gly Leu Leu Pro Val Arg Trp Met
210                 215                 220

Ala Pro Glu Ser Leu Lys Asp Gly Val Phe Thr Thr Ser Ser Asp Met
225                 230                 235                 240

Trp Ser Phe Gly Val Val Leu Trp Glu Ile Thr Ser Leu Ala Glu Gln
                245                 250                 255

Pro Tyr Gln Gly Leu Ser Asn Glu Gln Val Leu Lys Phe Val Met Asp
                260                 265                 270

Gly Gly Tyr Leu Asp Gln Pro Asp Asn Cys Pro Glu Arg Val Thr Asp
                275                 280                 285

Leu Met Arg Met Cys Trp Gln Phe Asn Pro Lys Met Arg Pro Thr Phe
290                 295                 300

Leu Glu Ile Val Asn Leu Leu Lys Asp Asp Leu His Pro Ser Phe Pro
305                 310                 315                 320

Glu Val Ser Phe Phe His Ser Glu Glu Asn Lys Ala Pro Glu Ser Glu
                325                 330                 335

Glu Leu Glu Met Glu Phe Glu Asp Met Glu Asn Val Pro Leu Asp Arg
                340                 345                 350

Ser Ser His Cys Gln Arg Glu Glu Ala Gly Gly Arg Asp Gly Gly Ser
                355                 360                 365

Ser Leu Gly Phe Lys Arg Ser Tyr Glu Glu His Ile Pro Tyr Thr His
                370                 375                 380

Met Asn Gly Gly Lys Lys Asn Gly Arg Ile Leu Thr Leu Pro Arg Ser
385                 390                 395                 400

Asn Pro Ser

<210> SEQ ID NO 5
<211> LENGTH: 11
<212> TYPE: PRT
<213> ORGANISM: Homo sapiens

<400> SEQUENCE: 5

Lys Thr Val Asn Glu Ser Ala Ser Leu Arg Glu
1               5                   10

<210> SEQ ID NO 6
<211> LENGTH: 13
<212> TYPE: PRT
<213> ORGANISM: Homo sapiens

<400> SEQUENCE: 6

Arg Phe Ala Arg Lys Gly Ala Leu Arg Gln Lys Asn Val
1               5                   10
```

PROTEIN KINASE C ANTAGONIST RELATED TO INSULIN RECEPTOR

STATEMENT AS TO FEDERALLY SPONSORED RESEARCH

This invention was made at least in part with funds from the Federal government through a grant from the National Institutes of Health, grant no. NIH DK 33649. The government may have certain rights in this invention.

BACKGROUND OF THE INVENTION

1. Field of the Invention

This invention relates to methods and compositions for the treatment of insulin resistance.

2. Description of Related Art

Insulin resistance is associated with several disease conditions including non-insulin dependent diabetes mellitus (NIDDM), obesity, hypertension, and cardiovascular disease. The most well-studies of these conditions is NIDDM. NIDDM, also termed maturity-onset diabetes or type II diabetes to differentiate it from insulin-dependent diabetes mellitus (IDDM, also termed type I or juvenile diabetes), usually occurs in middle-aged obese people and accounts for 80% to 90% of diagnosed diabetes. In addition to insulin resistance, NIDDM is associated with normal to elevated levels of insulin, hyperglycemia, increased levels of very low density lipoproteins (VLDL), and decreased muscle uptake of glucose. NIDDM is often associated with hypertriglyceridemia. Ketoacidosis, characteristic of IDDM, is not associated with NIDDM except when the patient is subjected to extreme stress (e.g., septic shock or myocardial infarction). NIDDM patients tend to develop many of the same complications associated with IDDM including nerve, eye, kidney, and coronary artery disease.

Mounting scientific evidence suggests that NIDDM results from a combination of two components: 1) a hereditary, genetic component (Rotter et al. In:: Rifkin et al., *Diabetes Mellitus: Theory and Practice.*, New York, Elsevier, 1990, pp. 378–413); and 2) an acquired component (Seely et al. In: Moller, Ed. *Insulin Resistance and Its Clinical Disorders*. England, John Wile & Sons, Ltd., 1993, pp. 187–252; Olefsky In: Efendic, et al. Eds. *New Concepts in the Pathogenesis of NIDDM*. New York, Plenum Publishing Corp., 1993; Olefsky, In: DeGroot, et al., Eds. *DeGroot Textbook of Endocrinology.*, 3rd Ed., Philadelphia, W. B. Saunders and Co., 1994). The genetic component of NIDDM is responsible for the first stage of the disease, termed the "prediabetic" state. The prediabetic state is characterized by hyperinsulinemia and "primary" insulin resistance. Insulin responsiveness in the prediabetic state is sufficient to maintain normal glucose tolerance (NGT) or at least impaired glucose tolerance (IGT).

As time passes, this compensatory mechanism fails in a subset of subjects, due to a decline in function of the insulin-producing β cells of the pancreas. The decline in insulin secretion, superimposed on the pre-existing genetic background, leads to the development of hyperglycemia, increased "secondary" insulin-resistance, and the final diabetic NIDDM state. The increase in insulin resistance in diabetic NIDDM relative to prediabetic NIDDM suggests that an additional, non-inherited factor creates a secondary component of insulin resistance that is additive to the inherited insulin resistance-inducing component present in the prediabetic state. This additional factor is hyperglycemia (Yki-Jarvinen, 1990, *Diabetologia*, 33:579–585; Yki-Jarvinen, 1992, *Endocrine Rev.*, 13:415–431).

The precise mechanism through which hyperglycemia induces insulin resistance is not understood. However, several observations have suggested that insulin resistance is due, at least in part, due to inhibition of the normal insulin receptor function. First, the hyperglycemic-NIDDM state leads to reduced insulin-stimulated activities including insulin receptor autophosphorylation, insulin receptor-mediated kinase activities (including tyrosine kinase), insulin-stimulated phosphatidylinositol kinase activity, and insulin-stimulated DNA synthesis (Freidenberg et al., 1987, *J. Clin. Invest.*, 79:240–250; Caro et al., 1986, *J. Clin. Invest.*, 78:249–258; Comi et al., 1987, *J. Clin. Invest.*, 79:453–462; Caro et al., 1987, *J. Clin. Invest.*, 79:1330–1337). Thus, although the receptor can bind insulin, the normal insulin-mediated transduction signals are not transmitted. The decrease in insulin receptor kinase activity has been correlated with the magnitude of the patient's hyperglycemia (Nolan et al., 1994, *J. Clin. Endocrinol. Metab.*, 78:471–477; Brillon et al., 1989, *Diabetes*, 38:397–403; Maegawa et al., 1991, *Diabetes*, 40:815–819).

Secondly, protein kinase C (PKC), which can phosphorylate serine and/or threonine residues, has been implicated in inactivation of insulin receptors in vitro. Incubation of cells under hyperglycemic conditions induces translocation and activation of PKC (Müller et al., 1991, *Diabetes*, 40:1440–1448; Mosthaf et al., 1993, *Exp. Clin. Endocrinol.*, 101(Suppl 2):150–151). Phorbol ester-mediated induction of PKC serine phosphorylation activity decreases insulin receptor kinase activity (Takayama et al., 1988, *J. Biol. Chem.*, 263:3440–3447). Hyperglycemia-induced inhibition of insulin receptor kinase activity is inhibited by incubation of cells with broad-based, non-specific PKC inhibitors such as staurosporin, H7, and polymyxin B (Mosthaf et al., supra).

The specific site of PKC-mediated phosphorylation is unknown. A better understanding of the cellular mechanisms underlying hyperglycemia-induced insulin resistance would greatly facilitate the design and development of specific therapeutics.

SUMMARY OF THE INVENTION

The invention is based on the discovery that hyperglycemia causes protein kinase C (PKC) to aberrantly phosphorylate a specific serine residue ($Ser_{1270}$) of insulin receptors. While phosphorylation of insulin receptor $Ser_{1270}$ does not significantly affect insulin binding, phosphorylation of $Ser_{1270}$ inhibits the insulin receptor's autophosphorylation and tyrosine kinase activities, thus inhibiting transduction of insulin-stimulated intracellular signals. The inability of the serine-phosphorylated insulin receptor to respond to insulin binding can result in insulin resistance.

In general, the invention features compositions, and methods for their identification and use in the inhibition of phosphorylation of insulin receptor residue $Ser_{1270}$ by protein kinase C (PKC).

In one aspect the invention features a protein kinase C antagonist having activity in inhibition of protein kinase C-mediated phosphorylation of $Ser_{1270}$ of an insulin receptor.

The invention also features a method of testing a candidate compound for PKC antagonist activity. According to the method, the candidate compound is contacted with i) protein kinase C and ii) a substrate for protein kinase C. A preferred substrate is a polypeptide derived from an insulin receptor, and containing amino acid sequences flanking $Ser_{1270}$. Compounds having PKC antagonist activity are identified by detecting a level of polypeptide substrate phosphorylation in the presence of the candidate compound.

In related aspects, the invention features a purified polynucleotide encoding a polypeptide having the amino acid sequence DDLHPSFPEVS (SEQ ID NO:1), with the proviso that polynucleotide does not encode a native insulin receptor, as well as vectors and transformed host cells containing the polynucleotide.

The invention additionally features therapeutic compositions composed of a PKC antagonist of the invention and a pharmaceutically acceptable carrier.

The therapeutic compositions of the invention can be used in a method of treating insulin resistance in a patient by administering a therapeutic composition containing a PKC antagonist in an amount effective to inhibit PKC-mediated serine phosphorylation of insulin receptors of the patient.

The invention further features a polynucleotide encoding a serine phosphorylation-resistant human insulin receptor, as well as vectors and host cells containing the polynucleotide.

The polynucleotide encoding a serine phosphorylation-resistant human insulin receptor can be used in a method of treatment of an insulin-resistant patient by genetically transforming cells of a patient with a construct containing the nucleotide sequence encoding a serine phosphorylation-resistant human insulin receptor, and a eukaryotic promoter sequence operably linked to the nucleotide sequence.

One advantage of the invention is that the PKC antagonists of the invention need only be delivered to insulin receptor-expressing cells in order to restore insulin sensitivity in the patient. Restoration of patient insulin sensitivity does not require complete inhibition of PKC-mediated insulin receptor serine phosphorylation, or even restoration of insulin receptor responsiveness in all insulin receptor-expressing cells.

Another advantage of the invention is that the polypeptide substrate of PKC serine phosphorylation (i.e., the insulin receptor polypeptide containing $Ser_{1270}$) provides a rationale basis for the design of drugs for the treatment of insulin resistance via the inhibition of PKC-mediated insulin receptor serine phosphorylation.

Still another advantage of the invention is that inhibition of PKC-mediated $Ser_{1270}$ phosphorylation serves as the basis for a rapid screening assay to identify candidate compounds which have activity as PKC serine phosphorylation inhibitors.

Other features and advantages of the invention will be apparent from the following description of the preferred embodiments thereof, and from the claims.

BRIEF DESCRIPTION OF THE DRAWINGS

FIGS. 2A–C shows the amino acid and DNA sequences of the cytoplasmic domain of the human insulin receptor.

FIG. 3 shows the amino acid sequence of in intracellular domain of the human insulin receptor (SEQ ID NO:4), and the amino acid residue position numbering used herein.

DETAILED DESCRIPTION

The invention is based on the discovery that hyperglycemia (i.e., a metabolic condition in which glucose accumulates in body fluids) causes protein kinase C (PKC) to aberrantly phosphorylate a specific serine residue ($Ser_{1720}$) of insulin receptors. While phosphorylation of the insulin receptor at the $Ser_{1270}$ residue does not significantly affect insulin binding, $Ser_{1270}$ phosphorylation inhibits the insulin receptor's autophosphorylation and tyrosine kinase activities. Because these insulin receptor kinase activities are essential in transduction of insulin-stimulated intracellular signals, serine-phosphorylated insulin receptor is unable to respond to insulin binding. Thus, serine-phosphorylation of insulin receptor by PKC results in insulin resistance, such as that associated with hyperglycemia in diabetic NIDDM patients.

Figure 1:
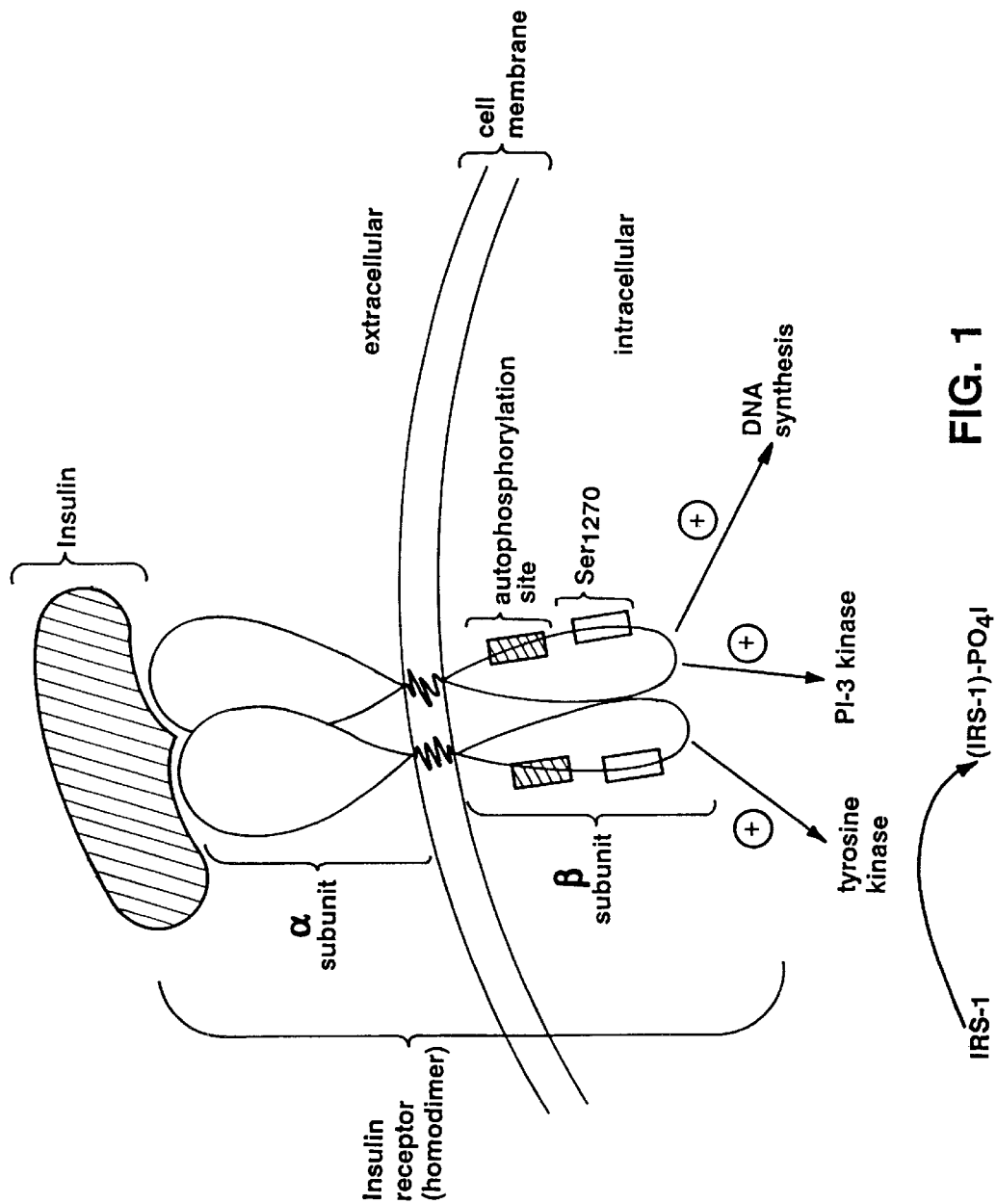
FIG. 1 is a schematic representation of the insulin receptor.

The insulin receptor is a homodimeric protein composed of two monomeric proteins which in turn are composed of α and β subunits. FIG. 1 is a rough, schematic representation of the insulin receptor, showing the relative position of the extracellular, transmembrane, and cytoplasmic domains, as well as the insulin receptor autophosphorylation sites and DDLHPSFPEVS (SEQ ID NO:1) sequences in the receptor.

The precise three-dimensional structure of the insulin receptor is not known. The amino acid and DNA sequences of the cytoplasmic domain of the human insulin receptor are shown in FIGS. 2A–C.

"$Ser_{1270}$" means the serine residue defined by the sequence DDLHPSFPEVS (SEQ ID NO:1), where the residue $Ser_{1270}$ is underlined. The residue position references used herein are those defined by the amino acid sequence numbering of the intracellular cytoplasmic domain of human insulin receptor as shown in FIG. 3.

"Protein kinase C" or "PKC" is an enzyme that facilitates phosphorylation of serine and threonine residues in a variety of proteins. PKC actually encompasses a family of at least 8 distinct PKC isoforms that can be present in various combinations according to cell type. For example, Rat 1 fibroblasts contain significant amounts of PKC alpha, beta, delta, and zeta.

"Hyperglycemia" means a dysfunctional metabolic state characterized by abnormally high glucose levels (e.g., >140 mg/dl) accompanied by normal to high levels of insulin. Hyperglycemia is modeled in vitro by incubation of insulin receptor-expressing cells in high glucose (20 mM to 25 mM) and normal to submaximal levels of insulin.

Protein Kinase C (PKC) Antagonists

"Protein kinase C antagonists" are compounds having inhibitory activity in PKC-mediated phosphorylation of the insulin receptor residue $Ser_{1270}$, particularly hyperglycemia-induced PKC-mediated serine phosphorylation. "Inhibitory activity in PKC-mediated phosphorylation of the insulin receptor residue $Ser_{1270}$" means that the PKC antagonist partially or completely inhibits PKC-mediated serine phosphorylation of the insulin receptor so as to maintain insulin receptor responsiveness to insulin binding under hyperglycemic conditions.

"Insulin receptor responsiveness to insulin binding" means that the insulin receptor responds to insulin binding by exhibiting at least one biological activity normally associated with insulin binding to the insulin receptor. Insulin binding-stimulated biological activities include, for example, insulin receptor autophosphorylation, insulin receptor-mediated tyrosine kinase and phosphatidylinositol kinase activities, and insulin-stimulated DNA synthesis.

PKC antagonists of the invention can inhibit PKC-mediated phosphorylation of insulin receptor $Ser_{1270}$ through a variety of mechanisms. For example, the PKC antagonist can inhibit PKC-mediated $Ser_{1270}$ phosphorylation through interaction with PKC (e.g., by binding to PKC, e.g., by reversible or nearly irreversible binding to a PKC catalytic site). Alternatively, the PKC antagonist can inhibit PKC-mediated $Ser_{1270}$ phosphorylation through interaction with the insulin receptor. For example, the PKC antagonist can bind to a peptide motif of the insulin receptor in a manner that masks PKC recognition of, or access to, the $Ser_{1270}$ residue. "Insulin receptor peptide motif" means an insulin receptor amino acid sequence with which another molecule (e.g., PKC or a PKC antagonist) interacts. PKC recognition of the $Ser_{1270}$ insulin receptor residue can be masked by the PKC antagonist by, for example, PKC antagonist binding to a peptide motif that encompasses $Ser_{1270}$ to directly block access of PKC to $Ser_{1270}$, by PKC antagonist binding to the insulin receptor that sterically hinders access of PKC to $Ser_{1270}$, or by binding to the insulin receptor in a manner that alters the three-dimensional structure (i.e., the conformation) of the peptide motif recognized by PKC, thus preventing PKC-insulin receptor interactions that promote phosphorylation of $Ser_{1270}$. PKC antagonist binding to the insulin receptor that alters the conformation of the $Ser_{1270}$ peptide motif can be to any portion of the insulin receptor (e.g., to either protein in the homodimer that constitutes the insulin receptor, and/or to the α and/or β subunits of an insulin receptor monomer). Without being bound to theory, PKC antagonists that interact with the insulin receptor are likely to interact with the β subunit, particularly with the DDLHPSFPEV (SEQ ID NO:1) peptide motif, which is in the β subunit.

Preferably, the PKC antagonists are peptidomimetic compounds. Peptidomimetic compounds are synthetic compounds having a three-dimensional structure based upon the three-dimensional structure (i.e., a "structural motif") of a selected peptide. Peptidomimetic compounds, which can be either peptide or non-peptide in composition, "mimic" peptides in that the compounds exhibit a similar or enhanced biological activity that is associated with the peptides, e.g., by binding to a catalytic site normally bound by the peptide.

Preferably, the peptidomimetic compounds of the invention have PKC antagonist activity that is substantially the same as, or greater than, the PKC antagonist activity of the peptide from which the peptidomimetic was derived. Preferred peptidomimetic PKC antagonists of the invention are derived from the amino acid sequence DDLHPSFPEVS (SEQ ID NO:1). The peptidomimetic compounds possess PKC antagonist activities that are substantially the same as, or greater than, the PKC antagonist activity of the peptide from which the peptidomimetics were derived.

Peptidomimetic compounds can have additional characteristics that enhance their therapeutic application, e.g., enhanced cell permeability, increased binding affinity and/or avidity for their respective target molecules, prolonged biological half-lives, and enhanced oral availability. The design of peptidomimetic compounds having PKC antagonist activity can be aided through computer modeling techniques well known in the art. Other methods for the design, as well as the preparation of, peptidomimetic compounds are well known in the art.

Further exemplary PKC antagonists of the invention include peptides having the insulin receptor amino acid sequence DDLHPSFPEVS (SEQ ID NO:1), or a substantially identical sequence. A "substantially identical sequence" is an amino acid sequence having at least 50%, preferably 85%, more preferably 90%, and most preferably 95% homology to the sequence DDLHPSFPEVS (SEQ ID NO:1)). Although the amino acid sequence DDLHPSFPEVS (SEQ ID NO:1) is derived from the amino acid residues 1265–1275 of the human insulin receptor (SEQ ID NO:4), the PKC antagonist can contain additional or fewer amino acid residues, provided that the peptides include the residue $Ser_{1270}$ (or an analog thereof). In general, where the PKC antagonist is a peptide, the peptide is composed of a portion of the native insulin receptor sequence. "Native insulin receptor sequence" means a nucleic acid sequence, or the amino acid sequence encoded thereby, which contains the entire wild-type insulin receptor sequence. For example, where the insulin receptor is a human insulin receptor, the native nucleic acid sequence encodes the amino acid sequence of naturally-occurring human insulin receptor in its entirety. Of particular interest are peptides that include the $Ser_{1270}$ residues as well as amino acid residues flanking $Ser_{1270}$ of the native human insulin receptor (SEQ ID NO:4).

Preferably, amino acid sequences substantially identical to the sequence DDLHPSFPEVS (SEQ ID NO:1) exhibit substantially the same or enhanced activity in inhibition of PKC serine phosphorylation activity (e.g., at least 25%, preferably at least 50%, more preferably at least 75%, even more preferably 90% to 100% or more of the activity of DDLHPSFPEVS (SEQ ID NO:1)). Exemplary peptides that are substantially similar to the peptide DDLHPSFPEVS (SEQ ID NO:1) are those having various amino acid substitutions (e.g., conservative substitutions), deletions, amino acid analogs (i.e., synthetic amino acid variants) or other modifications including chemical modifications (e.g., methylation, halogenation, etc.), yet retain the ability to inhibit PKC-mediated serine phosphorylation of the insulin receptor. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. Peptides having PKC antagonist activity can also contain D-amino acid substitutions. Of particular interest are peptide modifications which increase the PKC binding affinity and/or avidity of the peptide relative to the PKC binding affinity and/or avidity (i.e., the strength of peptide binding to PKC, e.g., the reversible or irreversible nature of PKC binding) of native insulin receptor.

In general, "peptide" means a chain of D- and/or L-amino acids, regardless of post-translational or chemical modification (e.g., glycosylation, phosphorylation, methylation, halogenation). "Peptides" contain considerably fewer amino acid residues than the polypeptides from which they were derived. Typically, peptides of the invention having PKC antagonist activity contain from about 2 to 100 amino acid residues, preferably from about 3 to 50 amino acid residues, more preferably from about 3 to 25 amino acids, still more preferably from about 5 to 20 amino acid residues, normally from about 5 to 15 amino acid residues, and generally contain about 11 amino acid residues, including residue $Ser_{1270}$ or a derivative thereof. Preferably, the peptides of the invention having PKC antagonist activity contain DDLHPSFPEVS (SEQ ID NO:1).

Identification of Protein Kinase C (PKC) Antagonists

The PKC antagonists of the invention are identified by their ability to inhibit PKC-mediated phosphorylation of the insulin receptor residue $Ser_{1270}$, particularly in a hyperglycemic environment.

PKC antagonists can be identified by, for example, their ability to: 1) inhibit PKC-mediated serine phosphorylation of insulin receptors in an in vitro hyperglycemia model; 2) inhibit PKC-mediated serine phosphorylation of a PKC substrate (e.g., an insulin receptor or other substrate containing DDLHPSFEVS (SEQ ID NO:1)) in a cell-free assay using purified PKC; or 3) competitively bind PKC in a cell-free, in vitro assay. Examples of each of these approaches to identification of PKC antagonist compounds is described in detail below.

I. PKC serine phosphorylation inhibition activity assays using whole cells

PKC antagonist compounds can be identified using insulin receptor-expressing cells in an in vitro assay that models the in vivo hyperglycemic state. The mammalian cells used in PKC antagonist assays can be any mammalian cell that expresses or overexpresses a functional insulin receptor (i.e., the insulin receptor exhibits insulin-stimulated activities found in normal insulin receptors).

The activity of the candidate PKC antagonist compounds is tested by introduction of the candidate compound into the cytoplasm of the mammalian cell. If the candidate compound can readily penetrate the mammalian cell membrane, the compound can be added to the medium bathing the mammalian cells prior to or during exposure of the cells to a high glucose environment with or without insulin. Exposure of the cells to high glucose and insulin serves as an in vitro model of the in vivo hyperglycemic state.

If the compound to be tested does not readily penetrate the mammalian cell membrane, the mammalian cells can be slightly permeabilized, e.g., by treatment with a non-lethal amount of a pore-forming compound such as a detergent, prior to incubation with the candidate compound. Alternatively, the candidate compound can be formulated to enhance its membrane permeability. For example, the candidate compound can be formulated in liposomes to enhance both delivery of the compound to the cells and introduction into the cell cytoplasm. Methods for the preparation of membrane-enhancing formulations are well known in the art (see e.g., Martin et al., 1982, J. Biol. Chem. 257:286–288; Szoka et al., 1980, Ann. Rev. Biophys. Bioeng. 9, 467–508, (1980); and Ostro, M. J. (ed) Liposomes From Biophysics to Therapeutics, Marcel Dekker, Inc., New York, 1987). Alternatively, the candidate compound can be microinjected directly into the cell cytoplasm using methods well known in the art.

Mammalian cells expressing a functional insulin receptor are incubated in either a normal glucose (e.g., about 5 mM glucose) or a high glucose environment (e.g., in the presence of 20 mM to 25 mM glucose) either with or without insulin. PKC antagonist compounds are identified by detecting a change in PKC-mediated serine phosphorylation activity. PKC-mediated serine phosphorylation activity in the cells can be monitored in many ways, including: a) directly detecting PKC-mediated serine phosphorylation of the insulin receptor; b) detecting insulin receptor autophosphorylation activity; c) detecting insulin receptor-mediated tyrosine kinase activity; d) detecting insulin-stimulated phosphatidylinositol kinase activity; or e) examining insulin-stimulated DNA synthesis.

A) Direct detection of serine phosphorylation of the insulin receptor

PKC-mediated serine phosphorylation of the insulin receptor can be directly assessed by incubating cells with a radionuclide, such as $^{32}P$, throughout the assay. Incorporation of the radionuclide in the insulin receptor due to phosphorylation, as well as the specific insulin receptor amino acids phosphorylated, are determined by phosphoamino acid and SDS-PAGE analysis. These techniques have been previously published (Anderson et al., 1991, J. Biol. Chem., 266:21760–21764; Sasaoka et al., 1994, J. Biol. Chem., 269:13689–13694). In the presence of a PKC antagonist of the invention, serine phosphorylation of the insulin receptor will be decreased under high glucose conditions relative to control samples without the PKC antagonist.

B) Detection of insulin receptor autophosphorylation activity

The effect of high glucose upon insulin receptor autophosphorylation, and the ability of the candidate compound to inhibit this effect, can be assessed by incubating cells with $^{32}P$ throughout the assay. Incorporation of the radionuclide in the insulin receptor due to autophosphorylation is determined by phosphoamino acid and SDS-PAGE analysis as described above. In the presence of a PKC antagonist of the invention, insulin receptor autophosphorylation will be increased under high glucose conditions relative to control samples without the PKC antagonist.

C) Detection of insulin receptor-mediated tyrosine kinase activity

Tyrosine kinase activity of the insulin receptor can be assessed by detecting phosphorylation of a substrate of this phosphorylation activity. For example, when insulin binds a functional insulin receptor, the protein IRS-1 (insulin receptor substrate-1) is tyrosine-phosphorylated by the insulin receptor. Thus, the level of tyrosine-phosphorylated IRS-1 can be correlated with the tyrosine kinase activity, and the normal function, of the insulin receptor.

If the candidate compound has PKC antagonist activity, then the percentage of BrDU positive cells under hyperglycemic conditions in the presence of 10 ng/ml insulin is increased relative to levels of BrDU incorporation in the absence of the PKC antagonist compound.

Table 1 summarizes the effects of the PKC antagonists on insulin-stimulated whole cells under normal or high glucose conditions during the in vitro assays described above.

TABLE 1

| Insulin Stimulation in the presence of: | | IR Serine Phosphorylation PKC Antagonist | | IR Auto-phosphorylation PKC Antagonist | | IR Tyrosine Kinase PKC Antagonist | | Insulin-stimulated PI-3 Kinase Activity PKC Antagonist | | Insulin-stimulated DNA Synthesis PKC Antagonist | |
|---|---|---|---|---|---|---|---|---|---|---|---|
| | | No | Yes | No | Yes | No | Yes | No | Yes | No | Yes |
| Normal Glucose | + | − | − | + | + | + | + | + | + | + | + |
| High Glucose | + | + | − | − | + | − | + | − | + | − | + |

*IR = insulin receptor

Tyrosine-phosphorylation of IRS-1 can be monitored by incubating cells with $^{32}$P throughout the assay. Incorporation of the radionuclide into IRS-1 can be detected by phosphoamino acid and SDS-PAGE analysis as described above, or by using anti-phosphotyrosine antibodies according to methods well known in the art. In the presence of a PKC antagonist of the invention, tyrosine phosphorylation of IRS-1 will be increased under hyperglycemic conditions relative to control samples without the PKC antagonist.

D) Detection of insulin-stimulated phosphatidylinositol (PI-3) kinase activity.

Insulin stimulation of cells also stimulates phosphatidylinositol (PI-3) kinase activity. PI-3 kinase activity can be detected using thin layer chromatographic analysis according to methods known in the art. In the presence of a PKC antagonist, PI-3 kinase activity will be higher under hyperglycemic conditions relative to control samples without the PKC antagonists.

E) Detection of insulin-stimulated DNA synthesis

In addition to insulin receptor autophosphorylation and IRS-1 tyrosine phosphorylation, insulin stimulation of cells via the insulin receptor results in increased DNA synthesis. Thus, hyperglycemia-induced inhibition of insulin-mediated signal transduction, and thus insulin receptor function, can be assessed by determining the relative levels of DNA synthesis in the absence or presence of insulin. In this assay, the mammalian cells are incubated in normal glucose (e.g., 5 mM) or high glucose (20 mM to 25 mM) media with or without the candidate compound. The cells are then stimulated with a submaximally effective insulin concentration (i.e., 10 ng/ml), and stained for incorporation of a molecular probe for DNA synthesis, e.g., bromodeoxyuridine (BrDU).

Normally, about 10% of the cells incorporate BrDU. In the presence of insulin under normal glucose levels, about 80% of cells will be stained with BrDU, with a half maximal effect at approximately 5–10 ng/ml insulin. In the presence of 25 mM glucose and 10 ng/ml insulin, BrDU incorporation is reduced by approximately 50%. For example, if 60% of cells are BrDU positive at 10 ng/ml insulin and physiological (5 mM) glucose conditions, then 10 ng/ml insulin in the presence of hyperglycemic (25 mM) glucose levels should result in reduction of the percentage of BrDU positive cells to about 25%.

II. Cell-free PKC antagonist assays

PKC-mediated serine phosphorylation of insulin receptors in a cell-free assay using purified, commercially available PKC and a substrate for PKC serine phosphorylation. The "PKC substrate" can be any substrate for PKC-mediated serine phosphorylation, preferably a polypeptide, more preferably a polypeptide having the amino acid sequence DDLHPSFPEVS (SEQ ID NO:1) of the insulin receptor. A preferred PKC substrate is purified insulin receptor, preferably a human insulin receptor, or a fragment thereof containing the amino acid sequence DDLHPSFPEVS (SEQ ID NO:1). Where the substrate is a peptide or polypeptide, PKC-mediated serine phosphorylation can be detected by phosphoamino analysis and/or SDS-PAGE analysis as described above. If the candidate compound has PKC antagonist activity, substrate serine phosphorylation is decreased in the presence of the candidate compound relative to levels of substrate serine phosphorylation in the absence of the candidate compound.

III. Competitive PKC binding assays

PKC antagonist compounds can be identified by assessing the ability of the compound to bind purified PKC in the presence of increasing concentrations of a polypeptide substrate of PKC serine phosphorylation, or of a previously identified PKC antagonist. The PKC polypeptide substrate, and peptides of the invention having PKC antagonist activity, preferably contain the amino acid sequence DDLHPSFPEVS (SEQ ID NO:1), or a PKC-binding derivative thereof.

The competitive binding assay is performed in a manner similar to competitive binding assays used in various immunodiagnostic assays. For example, the PKC polypeptide substrate is detectably labeled, e.g., by attachment of a fluorochrome (e.g., fluorescein) or a radiolabel. A known amount of the detectably labeled PKC polypeptide substrate is mixed with purified PKC and the candidate compound. Polypeptide substrate-PKC complexes are then isolated, and the amount of detectable label associated with these complexes determined. If the level of detectable label is decreased in the presence of the candidate compound, then the candidate compound has PKC antagonist activity.

As in competitive binding assays used in immunodiagnostic techniques, one of ordinary skill in the art can readily recognize that the PKC competitive binding assay described herein can be performed in a variety of ways. For example, the assay can be performed in solution or using a solid support (e.g., a microtiter well having PKC bound to its surface).

Animal Models of NIDDM

The in vivo efficacy of PKC antagonists of the invention can be readily assessed using an animal model of NIDDM, several of which are well known and accepted in the art as a model for NIDDM in humans.

For example, the insulin resistance of NIDDM in humans can be simulated in normal rats by giving an 8 hr glucose and low dose somatostatin infusion to make them hyperglycemic (about 250 mg/dl). These rats become significantly insulin resistant as measured by the glucose clamp technique. Thus exogenously-induced insulin resistance in the rat model can develop over a relatively short time frame, providing a hyperglycemic animal model useful for determining the in vivo effects of candidate PKC antagonist compounds.

Sources and/or Synthesis of PKC Antagonists

The PKC antagonists can be produced and/or isolated using a variety of techniques known in the art. For example, PKC antagonists can be isolated from a naturally-occurring source (e.g., a plant or microorganism), generated using chemical synthesis, or identified from a library of chemical compounds (e.g., chemical collections and/or combinatorial libraries available from commercial sources such as Merck)). Where the PKC antagonist is a peptide, the peptide can be produced by chemical synthesis or by recombinant DNA techniques (e.g., expression of DNA encoding the peptide of the invention in a prokaryotic or eukaryotic host cell). Methods for the synthesis of chemical compounds, including peptides, are well known in the art, as are methods for purification and isolation (see, for example, see, Deutscher, ed., 1990, "Guide to Protein Purification," Academic Press, Inc., San Diego, Calif., for purification of peptides).

Chemical Synthesis of Peptides for Use as PKC Serine Phosphorylation Substrates or PKC Antagonists PKC antagonist compounds and polypeptide substrates based on the amino acid sequences described herein and variations thereof can be synthesized using chemical synthesis methods well known in the art (see, for example, *Peptide Synthesis Protocols* (Methods in Molecular Biology, 35), Pennington and Dunn, eds., 1994, Humana Press, Totowa, N.J.; *Sold Phase Peptide Synthesis*, 2nd ed., Stewart et al., 1984, Pierce Chemical Company, Rockford, Ill.; *Peptides: Design, Synthesis, and Biological Activity,* Basava and Anantharamaiah, eds., 1994, Birkhäuser, Boston, Mass.; Jones, 1994, *The Chemical Synthesis of Peptides,* Clarendon Press, Oxford, England). For example, the PKC antagonist compounds can be synthesized by standard solid-phase methods using the tert-butyloxy-carbonyl and benzyl protection strategy described in Clark-Lewis et al., *P.N.A.S., USA,* 90:3574–3577 (1993) and Clark-Lewis et al., *Biochemistry,* 30:3128–3135 (1991). After deprotection with hydrogen fluoride, the proteins are folded by air oxidation and purified by reverse-phase HPLC. Purity is determined by reverse-phase HPLC and isoelectric focusing. Amino acid incorporation is monitored during synthesis, and the final composition is determined by amino acid analysis. The correct covalent structure of the protein can be confirmed using ion-spray mass spectrometry (SCIEX APIII).

After synthesis, the peptides having PKC antagonist activity can be cyclized by, for example, the formation of an additional carbon-carbon bond between the alpha carbons of the N-terminal amino acid and the C-terminal amino acid, according to the methods known in the art (see, for example, Mergler, 1994, *Meth. Mol. Biol.,* 90:287–301; Kates et al., 1995, *Tetrahedron Lett.,* 34:1549–1552; Cavelier-Frontin et al., 1993, *J. Mol. Struc.,* 286:125–130; Brady et al., 1979, *J. Org. Chem.,* 44(18):3101; McMurray et al., 1994, *Peptide Res.,* 7:195).

Recombinant DNA Techniques for Synthesis of Peptides or Polypeptides for Use as PKC-mediated Serine Phosphorylation Substrates or as PKC Antagonists Peptides or polypeptides for use as PKC-mediated serine phosphorylation substrates or as PKC antagonists of the invention can be produced using conventional molecular cloning and expression techniques that are well known in the art. As the first step in recombinant production of peptides and/or polypeptides, a polynucleotide encoding the peptide or polypeptide of interest is isolated and inserted into a cloning vector. "Purified polynucleotide" means nucleic acid (e.g., DNA or RNA) that is free of the nucleic acid sequences which, in the naturally-occurring genome of the organism from which the polynucleotide of the invention is derived, flank the peptide- or polypeptide-encoding nucleic acid, or any other episomal or chromosomal DNA naturally associated with the peptide- or polypeptide-encoding nucleic acid. The term thus includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional peptide sequences.

Methods for identification, cloning, and expression of DNA fragments encoding a sequence of interest are routine and well known in the art (see, for example, Sambrook et al., 1989, *Molecular Cloning: A Laboratory Manual,* 2nd Ed., Cold Spring Harbor Laboratory Press, Cold Spring Harbor, N.Y.). For example, DNA encoding insulin receptor peptides or polypeptides can be isolated from DNA encoding an insulin receptor using standard polymerase chain reaction (PCR) amplification of synthetic oligonucleotide primers, e.g., as described in Mullis et al., U.S. Pat. No. 4,800,159. While the DNA used to generate peptides or polypeptides for use in the invention can be any insulin receptor-encoding DNA, DNA encoding a human insulin receptor is preferred. In particular, DNA encoding a cytoplasmic domain of a human insulin receptor is preferred. Either of the two subtypes of the human insulin receptor can be used in the invention as these subtypes have identical or nearly identical β-subunits, which constitute the cytoplasmic domain (see FIGS. 2A–C and 3).

The gene encoding the human insulin receptor has been identified and cloned (Chen, 1985, *Nature,* 313:756–761). PCR amplification of insulin receptor-encoding DNA can be designed so as to generate polynucleotides encoding the insulin receptor residue $Ser_{1270}$, as well as amino acids flanking the $Ser_{1270}$ residue. The sequence of the primers for use in this PCR amplification techniques can be designed based upon the DNA sequence of, for example, the human insulin receptor (SEQ ID NO:4).

The peptide- or polypeptide-encoding polynucleotide is inserted into a vector so that the polynucleotide is operably linked to a promoter. Numerous vectors suitable for stable transformation of mammalian, yeast and bacterial cells are available to the public from a wide variety of sources, e.g., the American Type Culture Collection, Rockville, Md. Suitable host cells, as well as methods for constructing stably transformed host cell lines, are also well known, e.g., Pouwels et al., 1985, *Cloning Vectors: A Laboratory Manual,* Ausubel et al., 1989, *Current Protocols in Molecular Biology,* John Wiley & Sons, New York; and Sambrook et al., supra. The choice of host cell, the method of transformation, and the choice of expression vehicle will depend on the host system selected.

A "promoter" is a minimal sequence sufficient to direct transcription to which it is operably linked. Promoters include promoter elements (e.g., enhancers) that are sufficient to render promoter-dependent gene expression controllable for cell-type specific, tissue-specific or inducible by external signals or agents; such elements may be located in the 5' or 3' regions of the native gene. "Operably linked" means that a DNA of interest (e.g., DNA encoding a peptide or polypeptide of interest) and a regulatory sequence(s) are connected in such a way as to permit gene expression of the DNA of interest when the appropriate molecules (e.g., transcriptional activator proteins) are bound to the regulatory sequence(s), thus facilitating production of, a recombinant protein, or an RNA molecule.

The vector containing PKC substrate- or PKC antagonist-encoding DNA is constructed using known techniques and is introduced into a prokaryotic, yeast, or eukaryotic cell using transformation techniques well known in the art. "Transformation" means a permanent genetic change induced in a cell following incorporation of new DNA (i.e., DNA exogenous to the cell). Where the cell is a mammalian cell, the permanent genetic change is generally achieved by introduction of the DNA into the genome of the cell. "Transformed cell" means a cell into which (or into an ancestor of which) has been introduced, by means of recombinant DNA techniques, a polynucleotide encoding a peptide or polypeptide of the invention.

Techniques for obtaining expression of exogenous DNA or RNA sequences in a host cell are well known in the art (see, for example, Bormal et al., 1987, *Proc. Natl. Acad. Sci. USA,* 84:2150–2154; Sambrook et al., supra; each of which are hereby incorporated by reference with respect to methods and compositions for expression of a DNA of interest).

Polypeptides that can serve as PKC serine phosphorylation substrates, as well as peptides having PKC antagonist activity, can also be isolated by expression cloning methods well known in the art (see, for example, Sambrook et al., supra). For example, cells transformed with a DNA expression library, i.e., a collection of clones containing various cDNA fragments operably linked to a prokaryotic promoter. Expression of a polypeptide substrate for PKC serine phosphorylation can be detected by incorporation of a radionuclide in the presence of purified PKC, and subsequent phosphoamino acid and/or SDS-PAGE analysis. Expression of a peptide that has PKC antagonist activity can be detected by assaying the culture supernatant and/or cell lysates using purified PKC or a portion thereof that binds a known PKC antagonist. Where the peptide in the expression library binds to the PKC or PKC portion, the peptide is selected for its potential inhibitory activity of PKC-mediated serine phosphorylation of the insulin receptor.

The nucleotide sequence of the peptide- or polypeptide-encoding DNA can be determined using methods well known in the art (see, for example, Sambrook et al., supra). Following sequence confirmation, the resulting plasmid clones are used to transform the desired host for expression of the peptide- or polypeptide-encoding DNA.

Expression of recombinant peptides and polypeptides (e.g., produced by any of the expression systems described herein) can be assayed by immunological procedures, such as Western blot, immunoprecipitation analysis of recombinant cell extracts, analysis of PKC-mediated serine phosphorylation of proteins in recombinant cell extracts, or PKC antagonist activity of recombinant cell extracts.

Modification of Peptides having PKC Antagonist Activity

Where the PKC antagonists of the invention are peptides, the PKC antagonists can be modified so as to enhance several characteristics desirable for such PKC antagonists including PKC binding affinity and/or avidity, therapeutic efficacy, biological half-life, membrane permeability, targeting specificity, pharmacompatability, pharmacokinetics, bioavailability and other characteristics that enhance the therapeutic efficacy of the PKC antagonists. Chemical modifications can be used to synthesize petidomimetics which exhibit desirable pharmacokinetic and bioavailability characteristics.

Production of Anti-PKC Antagonist Antibodies

Polyclonal antibodies and/or monoclonal antibodies that specifically bind PKC antagonists, particularly peptides that are PKC antagonists, can be generated according to methods well known and routine in the art (see, for example, Harlow and Lane, 1988, *Antibodies: A Laboratory Manual,* Cold Spring Harbor Laboratory Press, Cold Spring Harbor, N.Y.; Schrier et al., 1980, *Hybridoma Techniques,* Cold Spring Harbor Laboratory Press, Cold Spring Harbor, N.Y.). Anti-PKC antagonist antibodies can be used in purification of the PKC antagonist and/or in assays to determine the activity of a specific PKC antagonist, e.g., through antibody binding and inhibition of the PKC antagonist in an in vitro assay.

Pharmaceutical Compositions

PKC antagonist compounds of the invention can be formulated in a pharmaceutical composition. A "pharmaceutical composition" means a composition appropriate for administration to a patient for use in a method of diagnosis or treatment. In general, pharmaceutical compositions of the invention contain a PKC antagonist and a pharmaceutically acceptable carrier.

A "pharmaceutically acceptable carrier" means a vehicle for delivering a PKC antagonist to a target cell, in which the vehicle is compatible with cell viability. Pharmaceutically acceptable carriers suitable for use in the administration of PKC antagonists of the invention are well known to those skilled in the art. Selection of the pharmaceutically acceptable carrier will depend upon a variety of factors including the PKC antagonist to be administered, the route of administration, and the condition to be treated.

Pharmaceutically acceptable carriers suitable for use with the PKC antagonists of the invention include, but are not limited to, 0.01–0.1 M and preferably 0.05 M succinate buffer or 0.8% saline. Additionally, such pharmaceutically acceptable carriers may be aqueous or non-aqueous solutions, suspensions, and emulsions. Further, pharmaceutically acceptable carriers may include detergents, phospholipids, fatty acids, or other lipid carriers. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils.

Pharmaceutically acceptable carriers for use with the PKC antagonists of the invention include lipid carriers. Lipid carriers can be in the form of sterile solutions or gels, or can be detergents or detergent-containing biological surfactants. Examples of nonionic detergents include polysorbate 80

(also known as TWEEN 80 or polyoxyethylenesorbitan monooleate). Examples of ionic detergents include, but are not limited to, alykltrimethylammonium bromide.

Where the pharmaceutically acceptable carrier is a lipid carrier, the lipid carrier may be a liposome. A liposome is any phospholipid membrane-bound vesicle capable of containing a desired substance, such as a PKC antagonist, in its hydrophilic interior. Appropriate lipids and other agents and methods for the preparation of therapeutic liposomes are well known in the art(see e.g., Martin, F. J. and Papahadjopoulos, D., *J. Biol. Chem.* 257:286–288, (1982); Szoka, F. and Papahadjopoulos, D., *Ann. Rev. Biophys. Bioeng.* 9, 467–508, (1980); and Ostro, M. J. (ed) *Liposomes From Biophysics to Therapeutics,* Marcel Dekker, Inc., New York, 1987). Intravenous vehicles include fluid and nutrient replenishers, electrolyte replenishers such as those based on Ringer's dextrose, and the like. Preservatives, other pharmaceutically active compounds, and other additives may also be present, such as, for example, antimicrobials, antioxidants, chelating agents, inert gases and the like.

Administration of PKC Antagonists

Patients amenable to treatment using the PKC antagonists of the invention include patients at any stage of NIDDM, including the prediabetic and diabetic states. Treatment of prediabetic NIDDM patients with PKC antagonists can serve to prevent the onset of secondary insulin resistance that results from prolonged hyperglycemia and the accompanying induction of PKC-mediated insulin receptor serine phosphorylation.

"Non-insulin dependent diabetes mellitus (NIDDM)" means an inheritable disease of glucose metabolism dysregulation characterized by insulin resistance, normal to elevated levels of insulin, hyperglycemia, increased levels of very low density lipoproteins (VLDL), and decreased muscle uptake of glucose. "Insulin resistance" means that the patient has high levels of blood glucose despite normal to high levels of insulin. According to the findings of the inventors, insulin resistance is mediated by the phosphorylation of $Ser_{1270}$ of the insulin receptor.

The therapeutic method of the invention involves administration of a therapeutic amount of a PKC antagonist to a prediabetic or diabetic NIDDM patient. "Therapeutically effective amount" means an amount of a composition effective to decrease the serine phosphorylation of insulin receptor by protein kinase C, thus restoring at least partial insulin responsiveness in the patient and facilitating the adjustment of blood glucose levels to sub-hyperglycemic levels (i.e., below about a fasting plasma glucose (PG) level of 140 mg/dl; and/or less than 200 mg/dl following a 75 g oral glucose tolerance test (OGTT)). Preferably therapeutic administration of PKC antagonists facilitates adjustment of the patient's blood glucose to blood glucose levels equated with impaired glucose tolerance (i.e., PG of about 140 mg/dl to 200 mg/dl 2 hr after a 75 g OGTT), more preferably to blood glucose levels equated with normal glucose tolerance (i.e., a fasting PG of less than about 140 mg/dl, and/or blood glucose levels less than about 140 mg/dl after at 2 hrs after a 75 g oral glucose load).

The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The route of administration and amount of PKC antagonist administered will vary widely according to the disease to be treated, and various patient variables including size, weight, age, disease severity, and responsiveness to therapy. Methods for determining the appropriate route of administration and dosage are generally determined on a case-by-case basis by the attending physician. Such determinations are routine to one of ordinary skill in the art (see, for example, *Remington's Pharmaceutical Sciences,* 18th ed., Gennaro, ed., Mack Publishing Company, Easton, Pa., 1990).

The specific dosage appropriate for administration is readily determined by one of ordinary skill in the art according to the factors discussed above (see, for example, *Remington's Pharmaceutical Sciences,* supra). In addition, the estimates for appropriate dosages in humans may be extrapolated from determinations of the level of PKC inhibitory activity determined in vitro and/or the amount of PKC antagonist effective in reducing insulin resistance in an animal model.

Routes of Administration of PKC Antagonists

Routes of administration of the PKC antagonists include, for example, oral, intravenous injection, liposome delivery, intraarterial delivery, and intramuscular delivery. For each route of administration, the PKC antagonist is formulated in a pharmaceutically acceptable carrier appropriate to the route of administration as determined by one of ordinary skill in the art. Preferably, the PKC antagonist is administered so as to target cells expressing insulin receptors. Classic insulin target tissues such as muscle (particularly skeletal muscle), fat, and liver cells are appropriate target cells for the delivery of PKC antagonists.

The PKC antagonists can also be administered in a controlled-release formulation. Controlled-release drug administration of an PKC antagonist means not only prolongation of the duration of drug delivery, similar to the objective in sustained release and prolonged release, but the term also implies the predictability and reproducibility of drug release kinetics.

Delivery Systems

Various delivery systems suitable for administration and intracellular delivery of the PKC antagonists are well known in the art. For example, the PKC antagonists can be administered using a dispersion delivery system. A dispersion system that can be used according to the invention is a synthetic membrane vesicle containing an PKC antagonist within the vesicle. The term "synthetic membrane vesicle" denotes a structure having one or more concentric chambers, commonly known as liposomes.

When phospholipids are dispersed in aqueous media, they swell, hydrate, and spontaneously form multilamellar concentric bilayer vesicles with layers of aqueous media separating the lipid bilayer. Such systems are usually referred to as multilamellar liposomes or multilamellar vesicles (MLVs) and have diameters ranging from about 100 nm to about 4 μm. When MLV's are sonicated, small unilamellar vesicles (SUVs) with diameters in the range of from about 20 nm to about 50 nm are formed, which contain an aqueous solution in the core of the SUV. The composition of the synthetic membrane vesicle is usually a combination of phospholipids, particularly high-phase-transition-temperature phospholipids, usually in combination with steroids, especially cholesterol. Other phospholipids or other lipids may also be used. (Szoka, et al., 1980, *Annual Reviews of Biophysics and Bioengineering,* 9:467; Deamer, et al., in *Liposomes,* Marcel Dekker, New York, 1983, 27; Hope et al., 1986, *Chem. Phys. Lipids,* 40:89).

According to the invention, therapeutic compositions containing PKC antagonists can also be administered orally.

Oral compositions may be taken in the form of solutions, suspensions, tablets, pills, capsules, sustained release formulas or powders. The pharmaceutical compositions formulated for systemic delivery via the oral route of administration irrespective of the mode of delivery (immediate, sustained, or controlled release) and the design of dosage forms (either solid, dispersion, or liquid), must be developed within the intrinsic characteristics of gastrointestinal (GI) physiology.

An example of one system for delivery of the compositions used in the method of the invention is an osmotic pressure-controlled gastrointestinal delivery system fabricated by encapsulating an osmotic core containing the agents within a semipermeable membrane made from biocompatible polymer, e.g., cellulose acetate. A delivery orifice with a controlled diameter is drilled, using a laser beam, through the coating membrane or controlling the release of agent solutes and capable of maintaining the structural integrity of the gastrointestinal delivery system during the course of the agent.

The external surface of the semipermeable membrane can also be coated with a layer of bioerodible polymer, e.g., enteric coating, to regulate the penetration of gastrointestinal fluid through the semipermeable membrane and target the delivery of agent to the lower region of the gastrointestinal tract.

Furthermore, the coating membrane of the delivery system can also be constructed from a laminate of two or more semipermeable membranes with differential permeabilities or a laminate of a semipermeable membrane and a microporous membrane (Great Britain Patent No. 1,556, 149) to modulate the rate of water influx and so program the rate of agent delivery.

Membrane permeation-controlled gastrointestinal delivery systems are also useful in the method of the invention. A microporous membrane permeation-controlled device is prepared by first compressing crystals (or particles) of water-soluble agent, in combination with appropriate pharmaceutical excipients, into a core tablet and then coating the tablet with a layer of non-GI-erodible polymer, e.g., a copolymer of vinyl chloride and vinyl acetate. The polymer coating contains a small amount of water-soluble pore-forming inorganic agents, e.g., magnesium lauryl sulfate, which create porosity when the tablet comes into contact with gastrointestinal fluid. Alternatively, the core tablet may be coated with a layer of non-GI-erodible thermoplastic polymer, e.g., polyvinyl chloride, which contains a high loading of plasticizer, e.g., dioctyl opthalate.

Another system well known in the art is the gastric fluid-resistant, intestine-targeted, controlled-release gastrointestinal delivery device. This device, which is designed to release a gastric fluid-labile agent only in the intestinal region at a controlled rate, is prepared by coating a core tablet of the agent with a combination of an intestinal fluid-insoluble polymer, e.g., ethylcellulose, and an intestinal fluid-soluble polymer, e.g., methylcellulose (or hydroxymethylcellulose phthalate).

The gel diffusion-controlled gastrointestinal delivery system is fabricated from gel-forming polymers. It can be prepared by first dispersing the therapeutic dose of the isomer in layers of water-soluble carboxymethylcellulose (CMC), sandwiching the agent-loaded CMC layers between layers of cross-linked carboxymethylcellulose (which is water insoluble, but water swellable) and then compressing these layers to form a multilaminated device.

A pH-controlled gastrointestinal delivery system is prepared by first blending an acidic (or basic) agent with one or more buffering agents, e.g., a primary, secondary, or tertiary salt of citric acid, granulating with appropriate pharmaceutical excipients to form small granules, and then coating the granules with a gastrointestinal fluid-permeable film-forming polymer, e.g., cellulose derivatives. Other GI delivery systems, such as ion-exchange-controlled gastrointestinal delivery systems, and hydrodynamic pressure-controlled gastrointestinal delivery systems are known to those of skill in the art.

Additional ingredients may be added to the therapeutic composition, as long as they are physiologically acceptable and not deleterious to the epithelial cells and their function. Such additives should not adversely affect the epithelial penetration efficiency of the above-noted enzyme inhibitors or stimulators, or degradation enzymes, nor cause the stability of the composition to deteriorate. Examples of ingredients which can be added to the compositions of the invention include stabilizers, preservatives, buffering agents, surfactants, emulsifiers, flavoring agents, fragrances, and the like.

The duration and frequency of the administration of a therapeutic composition can vary widely depending upon the a variety of factors including the magnitude of hyperglycemia (and thus the magnitude of insulin resistance), patient tolerance, patient responsiveness, and other factors well recognized in the art. Typical dosages can be from one unit dose up to a continuous contacting dose over a period of from one to several days. Thus, the contacting can follow a variety of regimens. Exemplary regimens include one or more brief unit doses administered over time as well as continuously administered doses for prolonged periods of from 5 minutes up to several hours or even days.

Dosages

The dose of each PKC antagonist is determined based on the guidance provided herein (e.g., the amount of PKC antagonist effective in PKC serine phosphorylation inhibition in vitro and/or dosages determined to be effective in increasing insulin sensitivity in animal models of hyperglycemia-induced insulin resistance as described herein). This guidance is combined with routine experimentation to optimize the dosage as necessary for the individual patient and specific cell being treated. Specific therapeutically effective amounts appropriate for administration are readily determined by one of ordinary skill in the art (see, for example, *Remington's Pharmaceutical Sciences,* 18th ed., Gennaro, ed., Mack Publishing Company, Easton, Pa., 1990).

Base therapy decreases serine phosphorylation mediated by PKC to provide a population of insulin-responsive receptors in the patient that allow maintenance of the normal glucose tolerance (NGT), or at least the impaired glucose tolerance (IGT) state. In vitro, the effective dosage range is determined by demonstration of inhibition of PKC-mediated serine phosphorylation of the insulin receptor. This is extrapolated to animal or human models by assuming a volume of distribution equal to total body water (body weight×0.7) and calculating the dosage in milligrams necessary to achieve the desired drug concentration. Where information is available on the $LD_{50}$, this determines the upper dosage limit. It is preferred to administer a dose 10-fold below the upper limit indicated by the $LD_{50}$.

Efficacious levels of administered PKC antagonists can be inferred from a variety of indicators for NIDDM. Preferably, efficacy of the PKC antagonist regimen is assessed by monitoring blood glucose levels in the NIDDM patient. Blood glucose monitoring is routine, and can be easily performed by the clinician or by the patient himself. Blood glucose levels that are decreased following PKC antagonist administration are indicative of patient response to therapy.

Serine Phosphorylation Resistant Insulin Receptors

The invention also features a method of treating insulin resistance in a patient by expressing in a patient, via gene therapy techniques, a polynucleotide encoding a serine phosphorylation resistant insulin receptor.

A "serine phosphorylation resistant insulin receptor" or "recombinant insulin receptor" as used herein means an insulin receptor that is not susceptible to inhibition of normal insulin receptor biological activities by PKC-mediated serine phosphorylation. Thus, under hyperglycemic conditions, serine-phosphorylation resistant insulin receptors bind insulin and exhibit insulin-stimulated insulin receptor activities at levels enhanced to those exhibited by native, serine phosphorylation susceptible insulin receptors. Serine phosphorylatino resisitant insulin receptors include derivatives of the native insulin receptor that contain amino acid substitutions, additions, deletions, and/or insertions as well as insulin receptor derivatives that are truncated relative to the wild-type protein, as long as these derivatives retain normal insulin receptor function, particularly normaly insulin receptor function under hyperglycemic conditions.

Preferably, the recombinant insulin receptor of the invention contains an amino acid substitution, insertion or deletion in the cytoplasmic domain of the insulin receptor (e.g., the β subunit) such that the insulin receptor peptide motif surrounding the $Ser_{1270}$ residue is no longer recognized by PKC, thus preventing PKC-mediated serine phosphorylation of the $Ser_{1270}$ residue. Preferably, the amino acid substitution, insertion, or deletion does not substantially affect insulin-stimulated insulin receptor biological activities (e.g., insulin receptor autophosphorylation, insulin receptor-mediated tyrosine kinase activity, insulin-stimulated PI-3 kinase activity, and insulin-stimulated DNA synthesis) under normal glucose or hyperglycemic conditions.

Preferably, the recombinant insulin receptor contains an amino acid substitution for the serine at residue position 1270. Amino acids suitable for substitution at residue position 1270 include any of the naturally occurring amino acids, preferably an amino acid that has side chain similar in length to that of serine and/or does not significantly affect the three-dimensional conformation of the insulin receptor (particularly the conformation of the insulin receptor cytoplasmic domain). Alanine is a preferred amino acid for substitution at $Ser_{1270}$. Thus, a recombinant insulin receptor of the invention has the same nucleotide sequence as native human insulin receptor, except for substitution of a codon encoding alanine (e.g., GCT, GCC, GCA, GCG) for the nucleotides encoding $Ser_{1270}$ (see FIGS. 2A–C for the nucleotide sequence of the human insulin receptor cytoplasmic domain).

A polynucleotide encoding any insulin receptor can be used to generate the serine phosphorylation resistant insulin receptors of the invention. Preferably the polynucleotide is a human insulin receptor-encoding DNA or a DNA molecule substantially identical thereto. "Substantially identical" means an amino acid or nucleic acid sequence exhibiting at least 50%, preferably 85%, more preferably 90%, and most preferably 95% homology to a reference amino acid or nucleic acid sequence. For amino acid sequences, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, and most preferably 110 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications.

A recombinant insulin receptor of the invention can be generated using recombinant nucleic acid techniques that are well known in the art (see, for example, Sambrook et al, supra). For example, a recombinant insulin receptor having an amino acid substitution for $Ser_{1270}$ can be generated using site-directed mutagenesis techniques well known in the art (see, for example, Sambrook et al., supra).

Serine phosphorylation resistant insulin receptors, and the polynucleotide encoding such receptors, suitable for use in gene therapy can be tested using the in vitro assays described above. For example, the polynucleotide encoding the serine phosphorylation resistant insulin receptor can be expressed in mammalian cells, and the function of the insulin receptor tested under normal glucose and hyperglycemic conditions in an in vitro assay. Recombinant insulin receptors that are not susceptible to inhibition by PKC-mediated serine phosphorylation are suitable for use in the gene therapy methods of the invention. Preferably, under hyperglycemic conditions, the recombinant insulin receptor exhibits insulin-stimulated biological activity that is substantially enhanced relative to the biological activity of native insulin receptor (e.g., serine phosphorylation susceptible insulin receptors) under hyperglycemic conditions.

Constructs for Expression of Serine Phosphorylation Resistant Insulin Receptors

Any nucleic acid construct having a eukaryotic promoter operably linked to a DNA of interest can be used to transform a target cell for serine-phosphorylation-resistant insulin receptor expression. A "construct" is a recombinantly produced nucleic acid molecule containing a polynucleotide of the invention. The constructs containing the DNA sequence (or the corresponding RNA sequence) that can be used in accordance with the invention can be any eukaryotic expression vector containing the DNA or the RNA sequence of interest, e.g., a plasmid or viral vector (e.g., adenovirus). Methods for manipulation of nucleic acid for preparation of constructs are well known in the art (see, for example, Sambrook et al., supra).

Various constructs (e.g., viral constructs, bacterial constructs, or constructs capable of replication in eukaryotic and prokaryotic hosts) can be used in accordance with the present invention. Preferably the construct is capable of replication in both eukaryotic and prokaryotic hosts. Numerous constructs which can replicate in eukaryotic and prokaryotic hosts are known in the art and are commercially available. In general, such constructs used in accordance with the invention are composed of a bacterial origin of replication and a eukaryotic promoter operably linked to a DNA of interest.

Preferably, the construct contains a promoter to facilitate expression of the recombinant insulin receptor of the invention within a targeted cell, preferably a skeletal muscle cell. Preferably the promoter is a strong, eukaryotic promoter. Exemplary eukaryotic promoters include promoters from cytomegalovirus (CMV), mouse mammary tumor virus (MMTV), Rous sarcoma virus (RSV), and adenovirus. More specifically, exemplary promoters include the promoter from the immediate early gene of human CMV (Boshart et al., *Cell* 41:521–530, 1985) and the promoter from the long terminal repeat (LTR) of RSV (Gorman et al., *Proc. Natl. Acad. Sci. USA* 79:6777–6781, 1982). Of these two promoters, the CMV promoter is preferred as it provides for higher levels of expression than the RSV promoter.

Other components such as a marker (e.g., an antibiotic resistance gene (such as an ampicillin resistance gene) or β-galactosidase) to aid in selection of cells containing and/or expressing the construct, an origin of replication for stable replication of the construct in a bacterial cell (preferably, a high copy number origin of replication), a nuclear localization signal, or other elements which facilitate production of the DNA construct, the protein encoded thereby, or both.

For eukaryotic expression (e.g., in a skeletal muscle cell), the construct minimally contains a eukaryotic promoter operably linked to a DNA encoding a recombinant insulin receptor of the invention, which is in turn operably linked to a polyadenylation sequence. The polyadenylation signal sequence can be selected from any of a variety of polyadenylation signal sequences known in the art. Preferably, the polyadenylation signal sequence is the SV40 early polyadenylation signal sequence. The construct can also include one or more introns, which can increase levels of expression of the DNA of interest, particularly where the DNA of interest is a cDNA (i.e., contains no introns of the naturally-occurring sequence). Any of a variety of introns known in the art may be used. For example, the intron can be the human β-globin intron inserted in the construct at a position 5' to the DNA encoding the serine phosphorylation resistant insulin receptor of the invention.

The construct containing DNA encoding a recombinant insulin receptor of the invention can also be designed to provide for site-specific integration into the genome of the targeted cell. For example, a construct can be produced such that the DNA of interest and the promoter to which it is operably linked are flanked by the position-specific integration markers of *Saccharomyces cerevisiae* Ty3. The construct for site-specific integration additionally contains DNA encoding a position-specific endonuclease which recognizes the integration markers. Such constructs take advantage of the homology between the Ty3 retrotransposon and various animal retroviruses. The Ty3 retrotransposon facilitates insertion of the DNA of interest into the 5' flanking region of many different tRNA genes, thus providing for more efficient integration of the DNA of interest without adverse effect upon the recombinant cell produced. Methods and compositions for preparation of such site-specific constructs are described in U.S. Pat. No. 5,292,662, incorporated herein by reference with respect to the construction and use of such site-specific insertion vectors.

Vectors for Expression of Serine Phosphorylation Resistant Insulin Receptors

A "vector" for transformation includes any compound, biological or chemical, that facilitates transformation of a target cell (e.g., a skeletal muscle cell) with a polynucleotide encoding a serine phosphorylation resistant insulin receptor. Exemplary biological vectors include viruses, particularly attenuated and/or replication-deficient viruses. Exemplary chemical vectors include, but are not limited to, naked polynucleotide constructs, viruses, plasmids, liposomal formulations, and polynucleotide constructs complexed with polycationic substances such as poly-L-lysine or DEAC-dextran. Methods for formulating biological and chemical vectors of the invention are well known in the art.

For example, DNA- or RNA-liposome complex formulations containing a polynucleotide encoding a recombinant insulin receptor of the invention can be composed of a mixture of lipids which bind to genetic material (DNA or RNA), providing a hydrophobic coat which allows the genetic material to be delivered into cells. Liposomes which can be used in accordance with the invention include DOPE (dioleyl phosphatidyl ethanol amine), CUDMEDA (N-(5-cholestrum-3-β-ol 3-urethanyl)-N',N'-dimethylethylene diamine). When the polynucleotide of the invention is introduced using a liposome, it is preferable to first determine in vitro the optimal values for the DNA:lipid ratios and the absolute concentrations of DNA and lipid as a function of cell death and transformation efficiency for the particular type of cell to be transformed. These values can then be used in or extrapolated for use in in vivo transformation. The in vitro determinations of these values can be readily carried out using techniques which are well known in the art.

The vector formulations can additionally include detergents, gelatins, capsules, or other delivery vehicles to protect against degradation, and/or targeting ligands, or other compounds that enhance targeting of the vector to a specific cell type and/or transformation of that cell type. For example, a chemical formulation of DNA or RNA encoding a recombinant insulin receptor of the invention can be coupled to a carrier molecule (e.g., an antibody or a receptor ligand) which facilitates delivery to host cells for the purpose of altering the biological properties of the host cells. "Chemical formulation" means modifications of nucleic acids to allow coupling of the nucleic acid compounds to a carrier molecule such as a protein or lipid, or derivative thereof. Exemplary protein carrier molecules include antibodies specific to the cells of a targeted cell or receptor ligands, i.e., molecules capable of interacting with receptors associated with a targeted cell.

The vector is prepared using known techniques to obtain a transformed cell capable of in vivo expression of a functional, serine phosphorylation resistant insulin receptor. The transformed cell is obtained by contacting a target cell with a RNA- or DNA-containing formulation permitting transfer and uptake of the RNA or DNA into the target cell, and, preferably, operative insertion of the DNA into the genome of the eukaryotic target cell. "Operative insertion" means that the DNA of interest is introduced into the target cell genome and is positioned adjacent a DNA sequence that directs transcription and translation of the introduced DNA (i.e., facilitates the production of the recombinant insulin receptor of the invention).

Where the vector is a viral vector, the viral vector is generally composed of a viral particle derived from a naturally-occurring virus that has been genetically altered to render the virus replication-defective and to express a recombinant insulin receptor in accordance with the invention. Once the virus delivers its genetic material to a cell, it does not generate additional infectious virus but does introduce exogenous recombinant genes into the cell, preferably into the genome of the cell.

Numerous viral vectors are well known in the art, including, for example, retrovirus, adenovirus, adeno-associated virus, herpes simplex virus (HSV), cytomegalovirus (CMV), vaccinia and poliovirus vectors. Selection of the appropriate viral vector is dependent upon various factors, including the relative rate of proliferation of the target cells type, the specific cell type targeted, and other factors recognized by one of ordinary skill in the art. For example, where the targeted cells are slowly replicating and/or terminally differentiated cells, retroviral vectors are less preferred (since retroviruses require replicating cells), and adenovirus is more preferred (since this virus efficiently infects slowly replicating and/or terminally differentiated cells).

Where a replication-deficient virus is used as the viral vector, the production of infective virus particles containing either DNA or RNA corresponding to the DNA of interest can be produced by introducing the viral construct into a recombinant cell line which provides the missing components essential for viral replication in trans. Preferably, transformation of the recombinant cell line with the recombinant viral vector will not result in production of replication-competent viruses, e.g., by homologous recombination of the viral sequences of the recombinant cell line into the introduced viral vector.

Methods for production of replication-deficient viral particles containing a DNA of interest are well known in the art and are described in, for example, Rosenfeld et al., *Science* 252:431–434, 1991 and Rosenfeld et al., *Cell* 68:143–155, 1992 (adenovirus); U.S. Pat. No. 5,139,941 (adeno-associated virus); U.S. Pat. No. 4,861,719 (retrovirus); and U.S. Pat. No. 5,356,806 (vaccinia virus).

Techniques for obtaining expression of exogenous DNA or RNA sequences in a host are known in the art (see, for example, Kormal et al., *Proc. Natl. Acad. Sci. USA*, 84:2150–2154, 1987; Sambrook et al., supra; each of which are hereby incorporated by reference with respect to methods and compositions for eukaryotic expression of a DNA of interest).

Administration of Vectors Containing Serine Phosphorylation Resistant Insulin Receptor-encoding Polynucleotides Introduction of a polynucleotide encoding a serine phosphorylation resistant insulin receptor of the invention into the genome of the targeted cell of the patient, e.g., a skeletal muscle cell of the patient, can be accomplished by various gene therapy methods well known in the art. In general, gene therapy (i.e., introduction of a DNA of interest into the patient's cells and expression therein to produce a protein of interest) is accomplished by either ex vivo or in vivo gene therapy methods. In in vivo gene therapy, target cell transformation can be accomplished by administering the polynucleotide directly to the patient. In ex vivo gene therapy, the polynucleotide is used to transform cells in an in vitro culture, preferably cells derived from a patient or other cell culture isolated from the patient. The transformed cells are subsequently transplanted into the patient. Methods for in vivo and ex vivo gene therapy are well known in the art (see, for example, U.S. Pat. No. 5,399,346 for methods for ex vivo gene therapy).

In vivo transformation methods normally employ either a biological means of introducing the DNA into the target cells (e.g., a virus containing the DNA of interest) or a mechanical means to introduce the DNA into the target cells (e.g., direct injection of DNA into the cells, liposome fusion, pneumatic injection using a "gene gun" (see for example, Fynan et al., 1993, *Proc. Natl. Acad. Sci. USA* 90:11478–11482). Generally the biological means used for in vivo transformation of target cells is a virus, particularly a virus which is capable of infecting the target cell, and integrating at least the DNA of interest into the target cell's genome, but is not capable of replicating. Such viruses are referred to as replication-deficient viruses or replication-deficient viral vectors. Alternatively, the virus containing the polynucleotide of the invention can replicate or replicate to a limited extent, but does not cause significant pathology or morbidity in the infected host (i.e., the virus is nonpathogenic or causes only minor disease symptoms). Exemplary viral vectors useful in in vivo transformation and gene therapy are known in the art, or can be readily constructed given the skill and knowledge in the art (e.g., non-replicative mutants/variants of adenovirus, retrovirus, adeno-associated virus, herpes simplex virus (HSV), cytomegalovirus (CMV), vaccinia virus, and poliovirus).

In vivo gene transfer using a biological means can be accomplished by administering the virus containing the DNA directly to the patient, e.g., by injection. The amount of DNA and/or the number of infectious viral particles effective to infect the targeted cell, transform a sufficient number of target cells, and provide for expression of serine phosphorylation resistant insulin receptor can be readily determined based upon such factors as the efficiency of the transformation in vitro, the levels of protein expression achieved in vitro, and the susceptibility of the targeted cells to transformation.

For example, DNA encoding a serine phosphorylation resistant insulin receptor of the invention can be delivered to the subject as, for example, purified DNA, a viral vector (e.g., adenovirus, retrovirus), a DNA- or RNA-liposome complex, or a DNA- or RNA-containing chemical formulation coupled to a carrier molecule which facilitates delivery to the targeted host cell.

The DNA or RNA molecule encoding a serine phosphorylation resistant insulin receptor of the invention can be administered either locally or systemically to the subject, which can be human or a non-human mammal (e.g., bovine, equine, canine, feline). For example, where the targeted cell is a skeletal muscle cell, administration of the DNA can be accomplished by local injection into or near skeletal muscle tissue. Systemic administration can be accomplished by intramuscular injection of a viral vector containing the DNA encoding a serine phosphorylation resistant insulin receptor of the invention.

Where gene therapy is accomplished by ex vivo methods, the in vitro cell culture (e.g., cells derived from a patient tissue biopsy) is transformed with a polynucleotide encoding a recombinant insulin receptor of the invention. Transformation can be accomplished by any of a variety of methods well known in the art including lipofection and infection with a viral vector containing recombinant insulin receptor-encoding DNA or RNA.

Where one or more selectable markers are transferred into the cells along with the polynucleotide of the invention, the cells containing the DNA of interest in the in vitro culture can be identified and enriched by selecting for the marker(s). Typically markers provide for resistance to antibiotics such as tetracycline, hygromycin, neomycin, and the like. Other markers can include thymidine kinase and the like.

The ability of the transformed target cells to express the DNA of interest can be assessed by various methods known in the art. For example, the ability of the cells to express the serine phosphorylation resistant insulin receptor on the cell surface can be examined by binding of a detectably labeled antibody to the insulin receptor on the cell surface. Alternatively, expression of the polynucleotide of the invention can be examined by Northern blot to detect mRNA which hybridizes with a DNA probe derived a selected sequence of the DNA, preferably a sequence that is unique to serine phosphorylation resistant insulin receptor of the invention. Those cells which properly express the polynucleotide of the invention can be further isolated and expanded in in vitro culture using methods well known in the art.

After expansion of the transformed cells in vitro, the cells are implanted into the patient, preferably into the tissue from which the cells were originally derived, by methods well known in the art. Preferably the cells are implanted in an area of dense vascularization, and in a manner that minimizes evidence of surgery in the subject. The engraftment of the implant of transformed cells is monitored by, for example, examining the patient for classic signs of graft rejection, i.e., inflammation and/or exfoliation at the site of implantation, and fever.

In general, the amount of recombinant insulin receptor-encoding polynucleotide, or the number of cells transformed in vitro with the polynucleotide of the invention will vary greatly according to a number of factors including the susceptibility of the target cells to transformation (e.g., in in vivo gene therapy), the size and weight of the subject, the success of survival of the implanted cells (e.g., in ex vivo gene therapy) and the levels of expression desired. For example, the amount of DNA injected into human skeletal muscle is generally from about 1 µg to 1,000 mg, preferably from about 100 µg to 500 mg, more preferably from about 500 µg to 100 mg, most preferably about 50 mg. Generally, the amounts of DNA for human gene therapy can be extrapolated from the amounts of DNA effective for gene therapy in an animal model. For example, the amount of DNA for gene therapy in a human is roughly 100 times the amount of DNA effective in gene therapy in a rat.

In general, the amount of recombinant insulin receptor-encoding polynucleotide delivered or the number of transformed cells implanted into the patient is an amount or number sufficient to restore insulin sensitivity to the patient. Restoration of patient insulin sensitivity does not require expression of serine phosphorylation resistant insulin receptors in all cells, or even in all skeletal muscle cells (in which tissue glucose metabolism is highest), of the patient.

Uses

The compositions and methods of the invention are useful in attenuation of insulin resistance and/or restoration of insulin sensitivity, in a patient through either inhibition of PKC-mediated phosphorylation of $Ser_{1270}$ of the insulin receptor, or expression of a serine phosphorylation resistant insulin receptor in the patient's cells.

The in vitro methods of the invention are useful for screening of candidate compounds for those which have activity in the inhibition of PKC-mediated phosphorylation of insulin receptor residue $Ser_{1270}$. Such an in vitro screen is commercially useful in rapidly identifying potentially useful compounds, and eliminating ineffective compounds from further study.

Another use of the PKC antagonists of the invention is as a PKC inhibitor reagent in medical and biochemical research applications. For example, the PKC antagonists of the invention could be used as a molecular probe to determine if a phenomenon observed either in vitro or in vivo is mediated by PKC. Several compounds having broad-based PKC inhibitory activity (e.g., H7, staurosporin, polymyxin B) are commercially available and are successful, important, viable research tools.

The following examples are intended to illustrate but not limit the invention. While they are typical of those that might be used, other procedures known to those of ordinary skill in the art may alternatively be used.

EXAMPLES

Example 1

Materials and Methods

Cell culture and materials

Rat1 fibroblasts stably transfected with and overexpressing either wild-type human insulin receptor (HIRcB) or mutant insulin receptors lacking the distal 43 amino acids of the β-subunit (ΔCT) were cultured in DME/F12 containing 500 nM methotrexate as described previously (McClain et al., 1988, *J. Biol. Chem.*, 263(18):8904–8911; Maegawa et al., 1988, *J. Biol. Chem.*, 263(18):8912–8917; McClain et al., 1987, *J. Biol. Chem.*, 262(30):14663–14671). Porcine insulin was purchased from Lilly. Enhanced chemiluminescence detection reagents were obtained from Amersham Corp.

Immunoblotting

HIRcB or ΔCT cells were cultured in 35 mm 6-well dishes and used in experiments at subconfluence. Approximately 16–24 h prior to experimental manipulations, the serum-containing media was removed and replaced with fresh serum-free DMEM (Sigma) containing 1 mM glucose. The appropriate amounts of glucose were then added for the periods indicated, and the cells stimulated with various ligands. Incubation was terminated by rapid aspiration of the medium followed by the addition of 100 µl Triton X-100 lysis buffer containing phosphatase and protease inhibitors. After a 10 min incubation, the lysates were clarified by centrifugation at 10,000×g and Laemmli sample buffer containing 5% mercaptoethanol was added to samples. The samples were boiled at 100° C. for 5 min and loaded onto 7.5% T/3%C Tricine-SDS PAGE gels. After electrophoresis, proteins were transferred to 0.45 µm nitrocellulose using a Bio-Rad SD Transblot.

The membrane was blocked for 1 h in 3% BSA in Tris-buffered saline (50 mM Tris, 150 mM NaCl, pH 7.4 with 0.1% Tween 20) (buffer A). The blocked membranes were probed with affinity-purified rabbit anti-phosphotyrosine antibody (0.5–1 µg/ml) in Tris-buffered saline (TBS) containing 0.1% BSA and 0.1% Tween 20 for 12 h, washed in TBS, 0.1% Tween 20, 1 mM EDTA (4×100 ml/10 min each) (buffer B), and then probed with anti-rabbit peroxidase conjugate (Amersham 1/1000) for 1 h. The membranes were then washed extensively in buffer B. Bound anti-phosphotyrosine antibody was detected using anti-rabbit peroxidase and the ECL reagent according to the manufacturer's instructions, and autoluminography on pre-flashed Kodak X-Omat AR film. Band intensities on the autoluminographs were quantified by densitometry on a Hewlett-Packard ScanJet II using Scananalysis software (Elseview Biosoft).

Microinjection of the protein kinase C inhibitor peptide

HIRcB or ΔCT cells were cultured on acid-washed glass coverslips, grown to semi-confluence, and then starved in serum-free DME with 1 mM glucose. The peptide was dissolved in microinjection buffer containing 5 mM $NaPO_4$ and 100 mM KCl, pH 7.4. The cells were microinjected with the PKC inhibitor peptide using glass capillary needles. Approximately 10 femtoliters of this solution was introduced into each cell. The injection included $1 \times 10^6$ molecules of IgG as marker for microinjection.

Two hours after microinjection, cells were incubated with BrDU plus various concentrations of growth factors for 16 h at 37° C. The cells were fixed with acid alcohol (90% ethanol, 5% acetic acid) for 20 min at 22° C., and then incubated with mouse monoclonal anti-BrDU antibody for 1 h at 22° C. The cells were then incubated with rhodamine-labeled donkey anti-mouse IgG antibody, and fluorescein isothiocyanate-labeled donkey anti-rabbit IgG antibody for 1 h at 22° C. to detect microinjected IgG and identify microinjected cells. After coverslips were mounted, the cells were analyzed and photographed with an Axiophot fluorescence microscope (Zeiss). Approximately 250–300 cells per coverslip were microinjected. Immunofluorescent staining of the injected cells indicated that about 75% of the cells were successfully microinjected.

Experiments using the cell-permeable PKC inhibitor Bisindolylmaleimide (GF 109203X; Calbiochem Biochemicals, San Diego, Calif., were performed by first dissolving the PKC inhibitor in DMSO at a stock concentration of 1 mM. HIRcB or ACT cells were grown on coverslips and serum-starved as described above. The cells were then incubated in high glucose (25 mM) for 18 h along with bisindolylmaleimide at a final concentration of 1 µM. During this period, the cells were stimulated with insulin followed by the addition of BrDU. BrDU incorporation was visualized using mouse anti-BrDU antibody and anti-mouse antibody conjugated to rhodamine as described above.

Two-dimensional phosphopeptide mapping

HIRcB cells were serum-starved for 16 h and then incubated in phosphate-free DMEM containing 2 mCi/ml $^{32}$P-orthophosphate for 3 h. The cells were then stimulated with high glucose (25 mM) or insulin as indicated. The cells were lysed, and the insulin receptor was immunoprecipitated using anti-phosphotyrosine antibody 83–14 as described. The washed immunoprecipitates were analyzed by SDS electrophoresis. The labeled β-subunit was visualized by autoradiography, excised from the gels and recovered by electroelution.

Polyacrylamide-gel pieces containing $^{32}$P-labeled IR and IRS-1 following in vitro phosphorylation were electroeluted in 20 mM Tris-HCl, pH 8.0, 2 mM EDTA, 0.1% SDS, and 0.1% 2-mercaptoethanol for 4 h. Eluted protein was precipitated with four volumes of acetone at −80° C. for 60 min followed by centrifugation at room temperature for 10 min at 10,000 g. The pellet was dried and digested with 10 µg of TPCK-treated trypsin (Worthington Diagnostic Systems, Freehold, N.J.) in 100 µl of 100 mM N-ethylmorpholine acetate (NMA), pH 8.2, for 24 h at 37° C. A further 10 µg of TPCK-treated trypsin was added and digestion continued for 12 h. The peptides were lyophilized, resuspended with water, and re-lyophilized at least three times. The $^{32}$P-labeled tryptic peptides were then resuspended in 5 µl of electrophoresis buffer and spotted onto thin layer cellulose plates. High voltage electrophoresis was performed in 1:3.5:40.5 formic acid/acetic acid/water, pH 1.9 using a Hunter thin layer electrophoresis system (C.B.S. Scientific, Del Mar, Calif.). Plates were subjected to ascending thin layer chromatography in the second dimension in 75:15:50:60 n-butanol/acetic acid/pyridine/water, dried, and then subjected to autoradiography at −80° C. on preflashed X-Omat AR film.

PI-3 kinase assays

Assays for insulin-stimulated phosphatidylinositol (PI-3) kinase activity were performed as described using anti-phosphotyrosine immunoprecipitates (Sadd et al., 1994, Mol. Endocrinol., 8(5):545–557) HIRc cells were exposed to high glucose and stimulated with insulin as described above. The cells were then lysed, and tyrosyl-phosphorylated proteins were precipitated using PY 20 (Transduction Labs, Lexington, Ky.) overnight. 100 µl of anti-mouse agarose was added to the lysates for 1 h. The agarose was sedimented by centrifugation and washed three times in the following buffers: i) 50 mM Tris; 150 mM NaCl; 1% NP40/Na$_3$PO$_4$; ii) 100 mM Tris pH 7.5/500 mM LiCl$_2$/100 µm Na$_3$PO$_4$; and iii) 10 mM Tris pH 7.5/100 mM NaCl/1 mM EDTA/100 µm Na$_3$PO$_4$. The bound immunoprecipitates were then assayed using soybean phospholipid (Sigma Chemical Company, St. Louis, Mo.) and $^{32}$P-ATP. The phosphorylated lipids were extracted with chloroform:methanol (1:1) and then separated by ascending chromatography on Silica gel 60 plates (EM Science) using chloroform:MEOH:NH$_4$OH:H$_2$0 (60:47:11.3:2). The labeled phospholipids were visualized by autoradiography and quantified by scintillation counting of the excised spots.

Example 2

Figure 4:
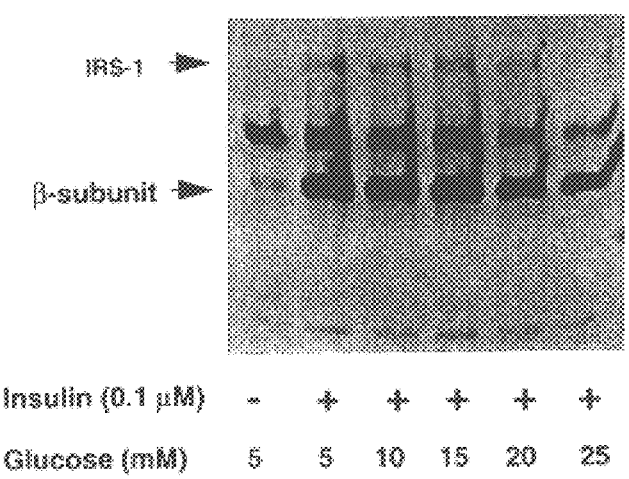
FIG. 4 is an autoradiograph showing the effect of increasing glucose concentration upon insulin receptor autophosphorylation (β-subunit) and insulin receptor-mediated insulin receptor substrate-1 (IRS-1) tyrosine phosphorylation in insulin-stimulated cells.
Figure 5:
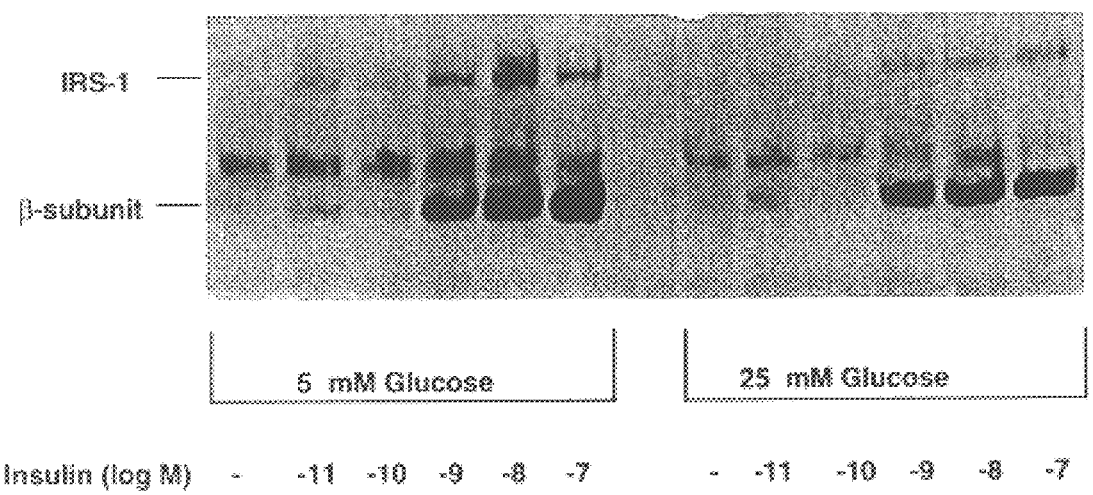
FIG. 5 is an autoradiograph showing the effects of stimulation of cells with submaximal concentrations of insulin in the presence of either normal glucose (5 mM) or high glucose (25 mM) upon insulin receptor autophosphorylation (β-subunit) and insulin receptor-mediated IRS-1 tyrosine phosphorylation.

Attenuation of Insulin-stimulated Tyrosine Phosphorylation of IRS-1 and the Insulin Receptor Exposure of cells to increasing concentrations of glucose ranging from 5–25 mM led to a progressive decrease in tyrosine autophosphorylation and IRS-1 tyrosine phosphorylation (FIG. 4). The predominant effect appeared to be on IRS-1, and to a lesser extent on insulin receptor autophosphorylation. This effect was also apparent at submaximal insulin concentrations as a shift in the dose-response curve for insulin-stimulation (FIG. 5).

Example 3

Specificity of hyperglycemia-induced Phosphorylation for the Insulin Receptor

Figure 6:
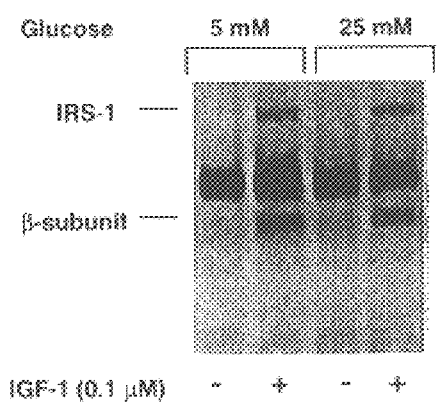
FIG. 6 is an autoradiograph showing the effects of normal glucose (5 mM) or high glucose (25 mM) upon insulin receptor autophosphorylation (β-subunit) and insulin receptor-mediated IRS-1 tyrosine phosphorylation in unstimulated or IGF-1-stimulated cells.

In order to determine whether high glucose specifically attenuated insulin receptor function, the effect of high glucose upon insulin-like growth factor-1 (IGF-1) stimulated IGF-1 receptor and IRS-1 phosphorylation was examined in HIRc cells. HIRc cells have high endogenous levels of IGF-1 receptors. Stimulation of β-subunit phosphorylation and IRS-1 phosphorylation was not affected by exposure to high glucose and IGF-1 (FIG. 6).

Example 4

Figure 7:
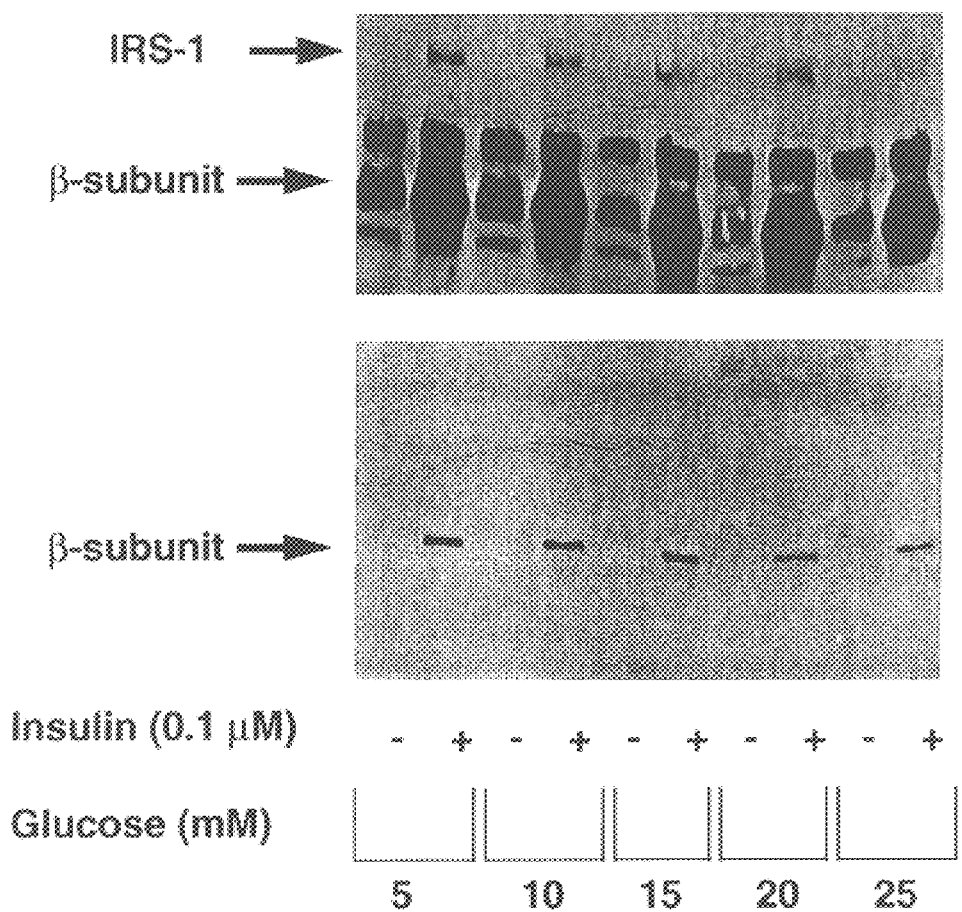
FIG. 7 is a collection of autoradiographs showing the effects of insulin stimulation and increasing glucose concentrations upon insulin receptor autophosphorylation (β-subunit) and insulin-receptor mediated IRS-1 tyrosine phosphorylation in cells expressing an insulin receptor lacking the distal 43 amino acids (ΔCT).

The Distal 43 Amino Acids of the Insulin Receptor do not Contain the Substrate Residue for Hyperglycemia-induced Phosphorylation Rat fibroblasts transfected with the mutant insulin receptor ΔCT were used to examine the structural features of the insulin receptor that facilitate high glucose-mediated insulin receptor inhibition (FIG. 7). The mutant ΔCT receptor lacks the distal 43 amino acids of the insulin receptor (amino acids 1311–1355 of FIG. 3). The distal 43 amino acids include the residues Thr$_{1348}$ and Ser$_{1327}$, which are phosphorylated in response to PMA stimulation with the PKC-activating phorbol ester PMA. Exposure of ΔCT-expressing cells to increasing glucose concentrations led to a dose-dependent decrease in insulin receptor β-subunit autophosphorylation, as well as IRS-1 phosphorylation (FIG. 7). Hyperglycemia-induced attenuation of insulin receptor β-subunit autophosphorylation and IRS-1 phosphorylation in ΔCT cells indicated that these effects are not mediated through the distal 43 amino acids, or specifically through phosphorylation of Thr$_{1348}$ and/or Ser$_{1327}$.

Example 5

Hyperglycemia-induced Phosphorylation is Mediated by PKC

Figure 8:
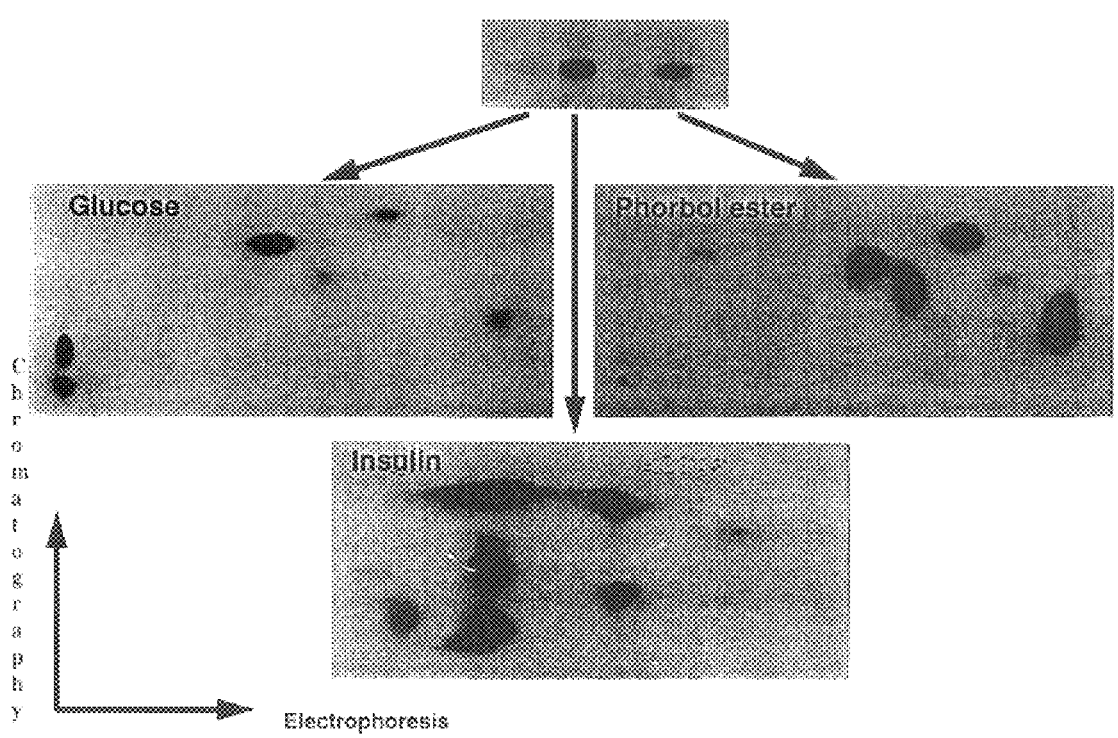
FIG. 8 are autoradiographs of two-dimensional tryptic phosphopeptide analysis of insulin receptor from cells exposed to high glucose alone (A), phorbol ester (B), or high glucose and insulin (C).

Although hyperglycemia leads to decreased insulin receptor kinase activity and activation of protein kinase C, it is possible that the effects of increasing glucose proceeds through a mechanism independent of protein kinase C. Two-dimensional tryptic phosphopeptide analysis of insulin receptors from cells exposed to PMA, or to high glucose and insulin, was performed to address this question (FIG. 8). Phorbol ester stimulation increased insulin receptor phosphorylation by 1.5-fold (FIG. 8). Analysis of phosphorylation patterns by two-dimensional tryptic phosphopeptide mapping revealed that the pattern of glucose-stimulated serine/threonine phosphorylation was similar, but not identical, to that induced by PMA. High glucose stimulated the phosphorylation of three distinct peptides, including one major and two minor peptides. In contrast, PMA stimulated the phosphorylation of four distinct peptides, three of which

Example 6
Effects of High Glucose on Insulin Receptor Phosphatidylinositol (PI-3)

Figure 9:
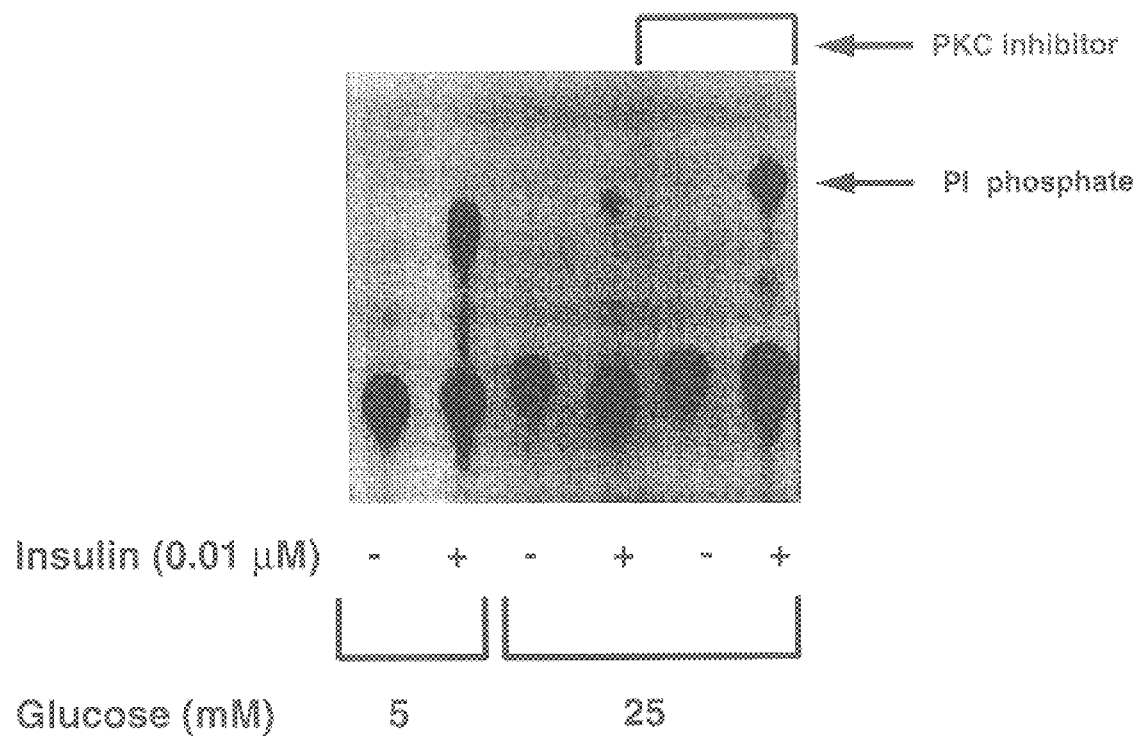
FIG. 9 is an autoradiograph showing the effects of insulin stimulation upon insulin-stimulated phosphatidylinositol kinase activity under either normal glucose (5 mM), high glucose (25 mM), or high glucose (25 mM) and the PKC antagonist bisindolylmaleimide.

Activation of protein kinase C in response to phorbol esters is known to inhibit insulin-stimulated PI-3 kinase activity. PI-3 kinase activity was examined in anti-phosphotyrosine immunoprecipitates of insulin-stimulated cells before and after preincubation with glucose. In cells exposed to 25 mM glucose for 1 h, insulin-stimulated PI-3 kinase activity was decreased by 80% (FIG. 9). Incubation of cells with a highly specific inhibitor of protein kinase C, bisindolylmaleimide, blocked this effect of high glucose.

Example 7
Effects of High Glucose on Insulin-stimulated Mitogenesis

Figure 10:
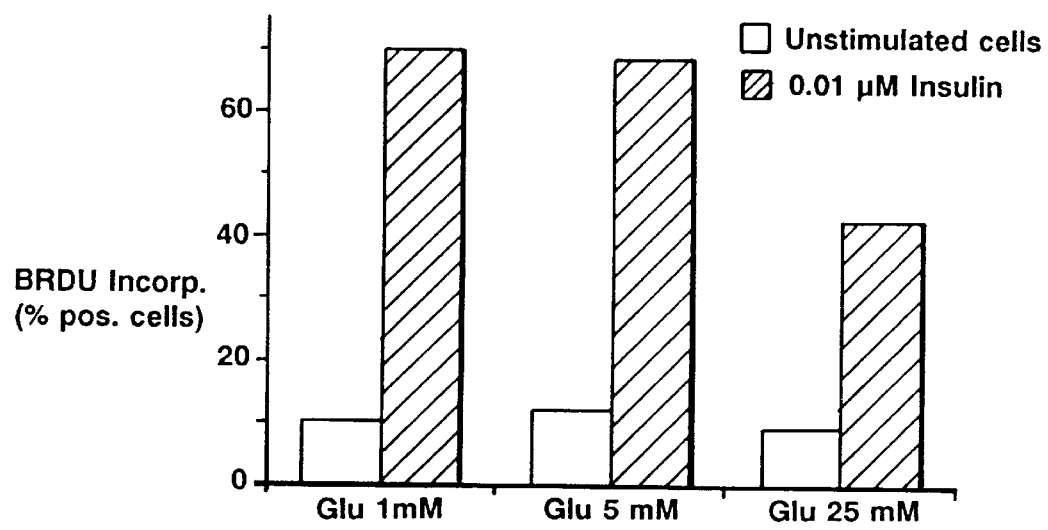
FIG. 10 is a graph showing the effect of insulin stimulation and increasing glucose concentrations upon DNA synthesis in the presence or absence of peptide 19–31.
Figure 11:
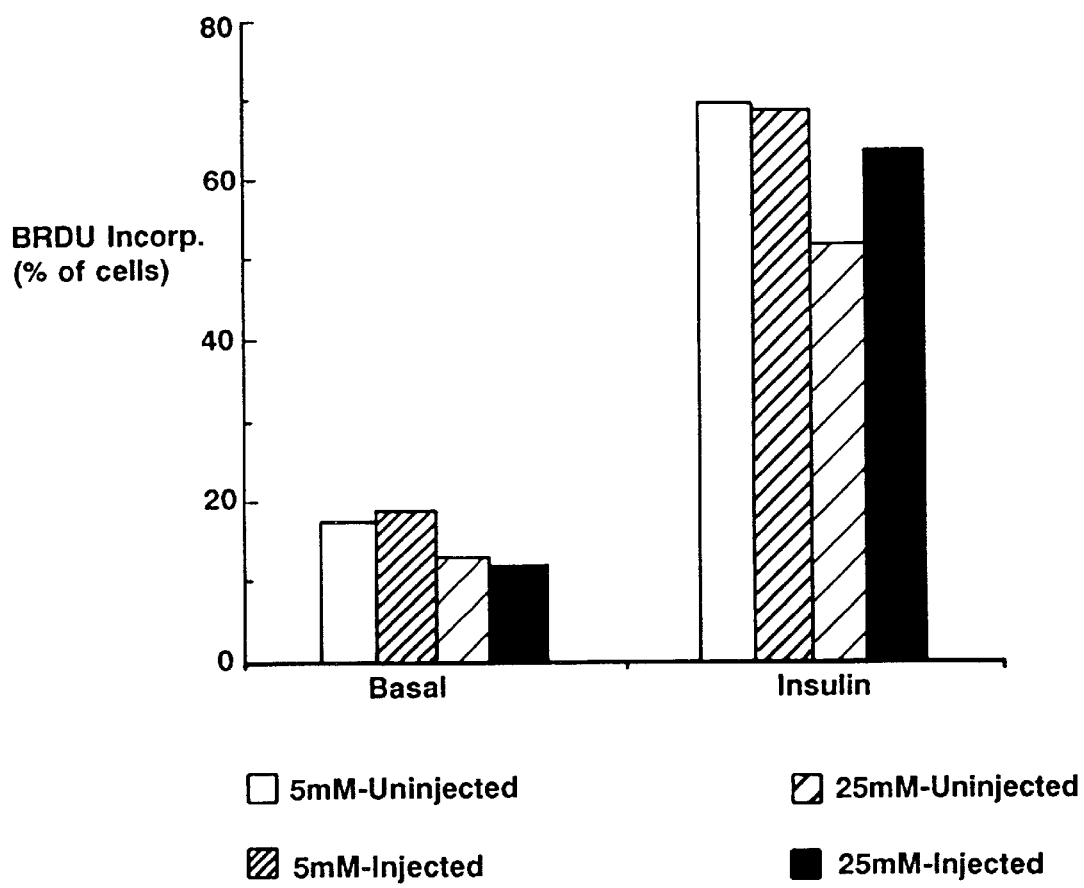
FIG. 11 is a graph showing the effects of the PKC inhibitor peptide 19–31 upon DNA synthesis in unstimulated (basal) or insulin-stimulated cells under normal glucose (5 mM) or high glucose (25 mM) conditions.

The effects of high glucose upon insulin-induced DNA synthesis were examined by first exposing cells to high glucose for 1 h, and then to insulin and BrDU for an additional 18 h. High glucose decreased DNA synthesis in insulin-stimulated cells by 30%, as measured by BrDU incorporation (FIG. 10). Co-incubation of the cells with the PKC inhibitor bisindolylmaleimide (data not shown), or microinjection of the PKC inhibitor Arg-Phe-Ala-Arg-Lys-Gly-Ala-Leu-Arg-Gln-Lys-Asn-Val (peptide 19–31) (SEQ ID NO:6) (Upstate Biotechnology Inc., Lake Placid, N.Y.) (FIG. 11), partially reversed inhibition of DNA synthesis.

Example 8
Hyperglycemia-induced Insulin Receptor Phosphorylation is not Mediated by MAP Kinases Stimulation of intact cells with PMA resulted in insulin receptor phosphorylation on sites in addition to those sites phosphorylated in purified insulin receptor exposed to purified protein kinase C. This suggests that additional kinases are activated in intact cells. Activation of protein kinase C results in activation of the Raf kinase→MAP kinase→cascade. The MAP kinases (ERK1 and ERK2) are serine/threonine kinases which may phosphorylate the insulin receptor and or IRS-1 in a negative feedback manner. This MAP→kinase-mediated serine/threonine phosphorylation may attenuate insulin-stimulated tyrosine phosphorylation.

Figure 12:
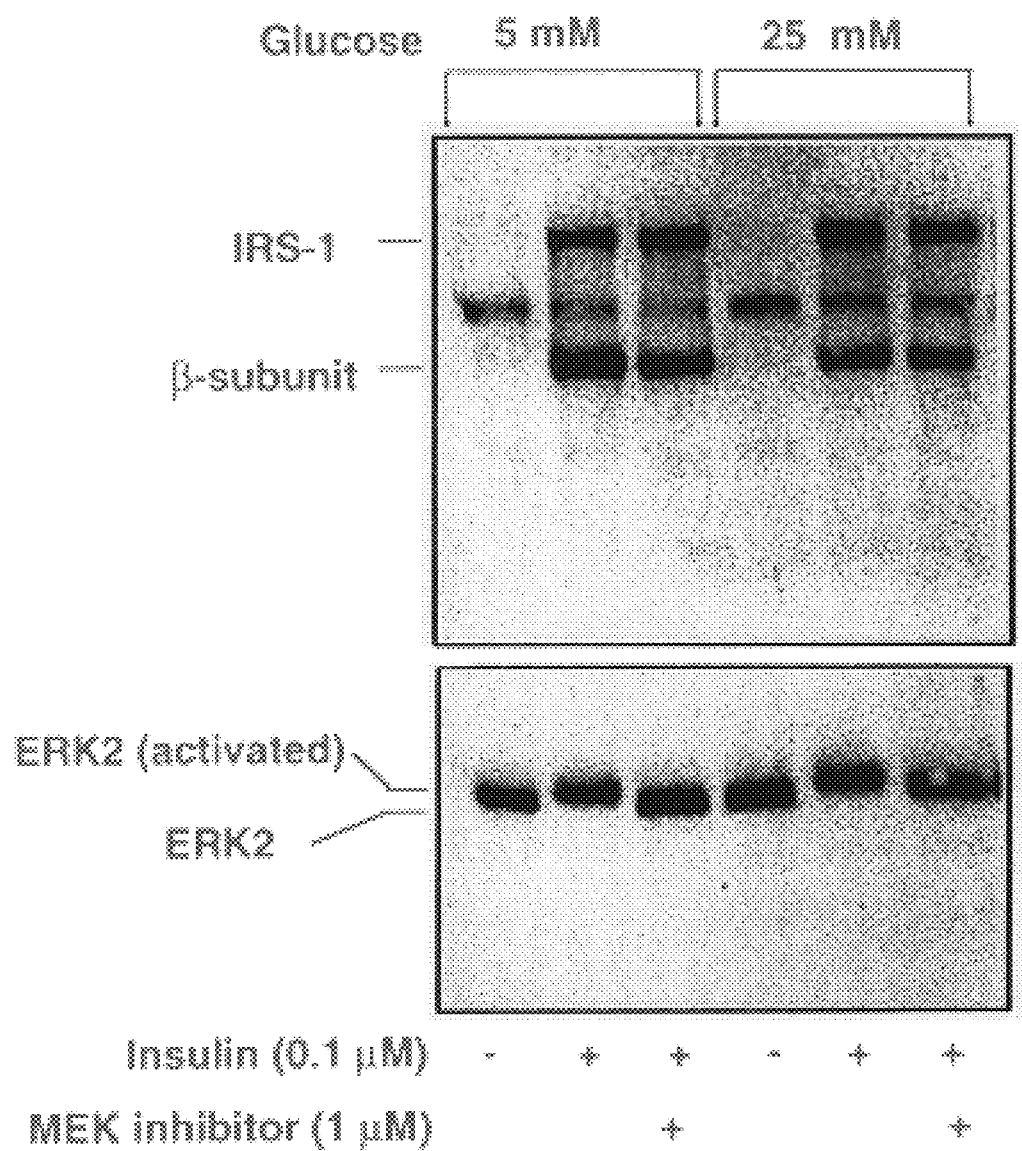
FIG. 12 are autoradiographs showing the effects of an MAP kinase kinase (MEK) inhibitor upon insulin receptor autophosphorylation and IRS-1 phosphorylation in unstimulated and insulin-stimulated cells under normal glucoe (5 mM) or high glucose (25 mM) conditions.

The role of the MAP kinase cascade was examined by exposing cells to a specific inhibitor of the MAP kinase kinase (MEK) in both normal and high glucose concentrations. Activation of ERK2 was confirmed by its change in mobility on SDS gel electrophoresis. Addition of MEK inhibitor did not reverse the impairment of insulin receptor and IRS-1 phosphorylation (FIG. 12). These data indicate that ERK activation does not result in impairment of insulin receptor or IRS-1 tyrosine phosphorylation.

Example 9
Microinjection of Peptides Derived from the Insulin Receptor

HIRcB cells were grown to sub-confluence on glass coverslips in D-MEM medium containing normal (5 mM) or high (25 mM) glucose and rendered quiescent by serum deprivation for 24 h. Synthetic cyclo-peptides were derived from the human insulin receptor, containing sequence KTVNESASLRE (SEQ ID NO:5) (Serine-1035) and DDLHPSFPEVS (SEQ ID NO:1) (Serine-1270) were synthesized using methods well known in the art. The peptides were dissolved in microinjection buffer containing 5 mM $NaPO_4$ and 100 mM KCl, pH 7.2, to a final concentration of 10 mM. All microinjected reagents contained rabbit IgG (5 mg/ml) to allow the identification non-injected cells. Samples were microinjected into the cell cytoplasm using an automated microinjection system at a typical needle pressure of about 100 hectopascals resulting in the introduction of $10^5$ molecules of IgG.

Approximately 1 h after microinjection, the cells were stimulated with 100 ng/ml insulin and 100 mM BrDU was added. Cells were incubated at 37° C. for an additional 16 h, and then fixed and stained using a monoclonal anti-BrDU antibody. Injected cells were identified with fluorescein isothiocyanate-conjugated donkey anti-rabbit IgG. Nuclear BrDU incorporation was detected with tetramethylrhodamine isothiocyanate-conjugated donkey anti-mouse IgG. The cells were analyzed by fluorescence microscopy. The approximately 300 cells microinjected on each coverslip, immunofluorescence staining indicated that about 90% were successfully microinjected.

Figure 13:
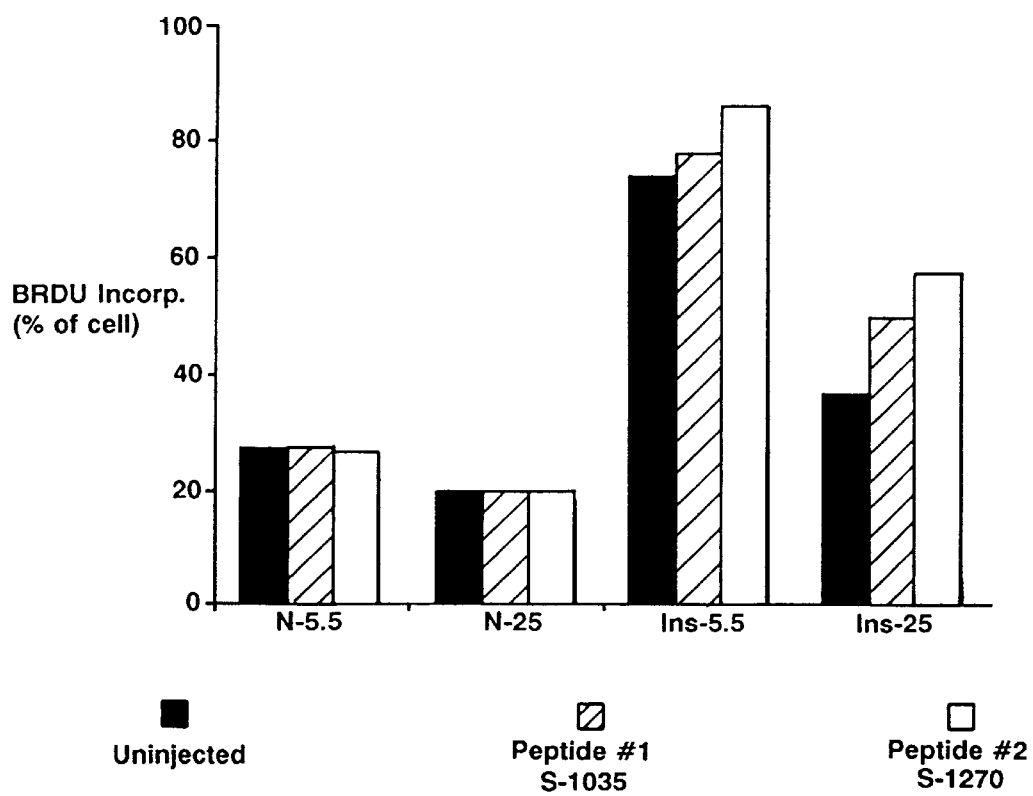
FIG. 13 is a graph showing the effects of microinjection of the peptide Ser-1035 (SEQ ID NO:5) or the peptide Ser-1270 (SEQ ID NO:1) upon DNA synthesis in unstimulated (N) or insulin-stimulated (Ins) cells under normal glucose (5 mM) or high glucose (25 mM) conditions.

Microinjection of either the Ser-1035 or the Ser-1270 peptides slightly increased DNA synthesis in insulin-stimulated cells under normal glucose conditions, and significantly increased insulin-stimulated DNA synthesis under high glucose conditions (FIG. 13). In each instance the increase in DNA synthesis in Ser-1270 peptide-injected cells was greater than in Ser-1035 peptide-injected cells. These data indicate that the peptide having a sequence similar to that of the Ser-1270 peptide inhibit PKC-mediated insulin receptor phosphorylation induced by hyperglycemic conditions.

The foregoing description of the invention is exemplary for purposes of illustration and explanation. It should be understood that various modifications can be made without departing from the spirit and scope of the invention. Accordingly, the following claims are intended to be interpreted to embrace all such modification.

All publications mentioned above are incorporated herein by reference (with the same effect as if each were individually incorporated by reference) for the purpose of describing and disclosing the cell lines, vectors, methodologies and other technologies described in the publications which might be used in connection with the invention described herein.

What is claimed is:

1. A protein kinase C (PKC) antagonist characterized by the ability to reduce the level of serine phosphorylation by protein kinase C of a substrate when contacted with protein kinase C and said substrate as compared to the level of serine phosphorylation by protein kinase C of said substrate in the absence of said antagonist, wherein said substrate is a peptide consisting of about 11 to 15 amino acids, wherein said peptide comprises the amino acid sequence of SEQ ID NO:1 or an amino acid sequence having at least 85% identity to SEQ ID NO:1.

2. A protein kinase C antagonist peptide consisting of amino acid sequence DDLHPSFPEVS (SEQ ID NO:1), wherein the peptide competitively inhibits protein kinase C-mediated phosphorylation of serine residue 1270 of an insulin receptor, which corresponds to residue 318 of SEQ ID NO:4.

3. A protein kinase C antagonist consisting of about 11 to 15 amino acids, wherein said antagonist comprises SEQ ID NO:1 or an amino acid sequence having at least 85% identity to SEQ ID NO:1, where the antagonist competitively inhibits protein kinase C-mediated phosphorylation of serine residue 1270 of an insulin receptor, which corresponds to residue 318 of SEQ ID NO:4 and wherein the antagonist maintains an insulin-stimulated insulin receptor activity selected from the group consisting of autophosphorylation activity, tyrosine kinase activity, phosphotidylinositol activity, and insulin-stimulated DNA synthesis.

4. The protein kinase C antagonist of claim 3, wherein the antagonist inhibits protein kinase C activity.

5. The protein kinase C antagonist of claim 3, wherein the antagonist binds to the protein kinase C catalytic binding site.

6. The protein kinase C antagonist of claim 3, wherein the antagonist binds to and masks serine residue 1270 of an insulin receptor, which corresponds to residue 318 of SEQ ID NO:4.

7. The protein kinase C antagonist of claim 3, wherein the antagonist binds to an insulin receptor peptide motif, and wherein the insulin receptor peptide motif is phosphorylated by protein kinase C.

8. The protein kinase C antagonist of claim 3, wherein the antagonist completely inhibits protein kinase C-mediated phosphorylation of serine residue 1270 of an insulin receptor, which corresponds to residue 318 of SEQ ID NO:4.

9. A method of identifying a compound having protein kinase C antagonist activity comprising:
   a) contacting a compound with protein kinase C and a substrate wherein said substrate is a peptide consisting of about 11 to 15 amino acids, wherein said peptide comprises the amino acid sequence of SEQ ID NO:1 or an amino acid sequence having at least 85% identity to SEQ ID NO:1, and wherein said peptide includes a serine flanked by at least 5 amino acids; and
   b) detecting the level of phosphorylation of serine residue 1270, corresponding to residue 318 of SEQ ID NO:4, of said substrate by protein kinase C in the presence of said compound as compared to the level of phosphorylation in the absence of said compound, wherein a reduced level of phosphorylation in the presence of said compound indicates that said compound has PKC antagonist activity.

10. The method of claim 9, wherein detecting is by measurement of a radionucleotide.

11. The method of claim 9, wherein said contacting is performed in a cell-free system.

12. The method of claim 9, wherein said substrate is a polypeptide having the amino acid sequence DDLHPSFPEVS (SEQ ID NO:1).

13. The method of claim 12, wherein said polypeptide is expressed by a polynucleotide encoding SEQ ID NO:1 in a mammalian cell.

* * * * *